(12) United States Patent
Xi et al.

(10) Patent No.: US 10,913,766 B2
(45) Date of Patent: **\*Feb. 9, 2021**

(54) LIVER SPECIFIC DELIVERY-BASED ENTECAVIR PRODRUG, NUCLEOSIDE CYCLIC PHOSPHATE COMPOUND, AND APPLICATION THEREOF

(71) Applicant: ZHEJIANG PALO ALTO PHARMACEUTICALS, INC., Quzhou (CN)

(72) Inventors: Zhijian Xi, Quzhou (CN); Huaqiang Xu, Quzhou (CN); Chunping Lu, Quzhou (CN); Zhongshan Wu, Quzhou (CN)

( * ) Notice: Subject to any disclaimer, the term of this patent is extended or adjusted under 35 U.S.C. 154(b) by 0 days.

This patent is subject to a terminal disclaimer.

(21) Appl. No.: 16/907,213

(22) Filed: Jun. 20, 2020

(65) Prior Publication Data

US 2020/0317713 A1 Oct. 8, 2020

Related U.S. Application Data

(63) Continuation of application No. PCT/CN2018/122824, filed on Dec. 21, 2018.

(30) Foreign Application Priority Data

Dec. 22, 2017 (CN) .......................... 2017 1 1408937

(51) Int. Cl.
| | | |
|---|---|---|
| C07H 19/213 | (2006.01) | |
| C07F 9/6571 | (2006.01) | |
| C07D 473/18 | (2006.01) | |
| C07H 19/11 | (2006.01) | |
| A61P 1/16 | (2006.01) | |

(52) U.S. Cl.
CPC ............... C07H 19/11 (2013.01); A61P 1/16 (2018.01); C07D 473/18 (2013.01); C07F 9/6571 (2013.01); C07H 19/213 (2013.01); C07B 2200/13 (2013.01)

(58) Field of Classification Search
None
See application file for complete search history.

(56) References Cited

U.S. PATENT DOCUMENTS

| | | | |
|---|---|---|---|
| 5,206,244 A * | 4/1993 | Zahler | ............... C07D 239/553 514/263.3 |
| 8,173,621 B2 | 5/2012 | Du et al. | |
| 10,668,090 B2 * | 6/2020 | Xi | ........................ A61K 31/675 |
| 2010/0302060 A1 | 12/2010 | Montgomery et al. | |
| 2016/0016986 A1 | 1/2016 | Deshpande et al. | |

FOREIGN PATENT DOCUMENTS

| | | |
|---|---|---|
| CN | 101475594 A | 7/2009 |
| CN | 105287419 A | 2/2016 |

OTHER PUBLICATIONS

Internation Search Report of PCT/CN2018/122824, dated Mar. 20, 2019.

* cited by examiner

*Primary Examiner* — Traviss C McIntosh, III
(74) *Attorney, Agent, or Firm* — W&K IP

(57) ABSTRACT

Disclosed is a liver specific delivery (LSD)-based entecavir antiviral prodrug, i.e., a nucleoside cyclic phosphate compound, and the application thereof. Specifically, disclosed are a compound as represented by formula (I) and isomers, pharmaceutically acceptable salts, hydrates, and solvates of the compound, and a corresponding pharmaceutical composition. Also disclosed is the application of the compound of the present invention, used separately or used in combination with other antiviral drugs, against viruses, especially the application against hepatitis B virus (HBV).

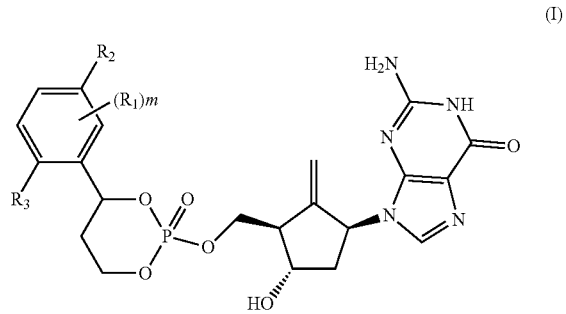

5 Claims, 3 Drawing Sheets

LIVER SPECIFIC DELIVERY-BASED ENTECAVIR PRODRUG, NUCLEOSIDE CYCLIC PHOSPHATE COMPOUND, AND APPLICATION THEREOF

CROSS-REFERENCE TO RELATED APPLICATIONS

The present disclosure is a continuation application of International Application No. PCT/CN2018/122824 filed Dec. 21, 2018, and claims priority to Chinese Application No. 201711408937.2 filed on Dec. 22, 2017, which are incorporated herein by reference.

TECHNICAL FIELD

The present disclosure relates to the preparation and use of a liver specific delivery (LSD)-based antiviral prodrug, a nucleoside cyclic phosphate compound, or an optical isomer, a hydrate, a solvate, a pharmaceutically acceptable salt or a pharmaceutical composition thereof.

BACKGROUND ART

Viruses such as hepatitis B virus (HBV), hepatitis D virus (HDV), human immunodeficiency virus (HIV) cause severe threats to human health. Taking hepatitis B virus as an example, viral hepatitis B (hepatitis B) is a disease that is caused by hepatitis B virus and characterized mainly by inflammatory lesions of the liver and that may lead to damage to multiple organs. According to World Health Organization (WHO) survey results, it is estimated that there are 240 million people infected with chronic hepatitis B in the world, and it is estimated that there are 780,000 deaths from hepatitis B infection every year, including 650,000 deaths from liver cirrhosis and liver cancer caused by chronic hepatitis B and 130,000 deaths from acute hepatitis B infection. Hepatitis B has been a critical and global health issue.

Anti-HBV drugs mainly include a class of nucleotide drugs such as adefovir dipivoxil, tenofovir disoproxil fumarate (TDF), tenofovir alafenamide (TAF), entecavir, lamivudine, telbivudine, etc. These drugs act through a mechanism of activation into triphosphate metabolites in cells to inhibit the DNA polymerase activity of the virus and prevent the synthesis of viral DNA, thereby inhibiting viral replication.

Anti-HBV nucleoside compounds include nucleotide analogs with monophosphate and nucleoside analogs without monophosphate. The nucleotide analogs such as adefovir and tenofovir are generally pharmaceutically prepared in the form of phosphate esters, such as adefovir dipivoxil and tenofovir disoproxil fumarate, which can be directly metabolized into monophosphate products in the body. The nucleoside analogs such as entecavir are pharmaceutically prepared directly as nucleoside analogs, which can be converted into monophosphate metabolites in the body via one-step phosphorylation, and the phosphorylation process is the rate-limiting step for their conversion into the final active form of triphosphate metabolites, resulting in lower effective active ingredients in the liver. Currently, no monophosphate prodrugs for entecavir are developed and commercially available.

Entecavir has extremely strong antiviral activity in vitro (EC50=0.004 μM), it is the most active compound in the prior art nucleoside drugs, and it also has strong inhibitory activity (EC50=0.010–0.059 μM) against lamivudine-resistant virus strains. Entecavir can inhibit all the following three activities of HBV polymerase: 1) the starting and initiation of HBV polymerase; 2) reverse transcription of pregenomic RNA for synthesis of the minus strand of rcDNA (a relaxed circular double-stranded DNA); 3) synthesis of the plus strand of rcDNA. In addition, the incidence of entecavir resistance is extremely low at 1.2% by year 6. It can be seen that entecavir has the advantages of strong antiviral activity and high barrier to drug resistance among the commercially available nucleoside drugs.

However, it has been clinically found that entecavir may cause side effects such as headache, fatigue, dizziness, and nausea. Its clinical application is limited by these side effects. For example, 1 mg specification of Baraclude (the trade name of entecavir) is recommended only for patients with lamivudine resistance, and a dosage of 0.5 mg is recommended for non-resistant patients.

In the present disclosure, the liver-specific delivery technology is utilized to bypass the kinase phosphorylation step, and the concentration of the active ingredient in the liver is successfully increased.

An entecavir prodrug modified with a cyclic phosphate is metabolized by CYP3A enzyme in the liver without producing a monophosphate compound in the presence of phosphokinase. Specifically, the structure of a cyclic phosphate (4-aryl-2-oxo-1,3,2-dioxaphosphorinane) precursor has good liver specific delivery performance and acts through a very clear mechanism. The 4-aryl-substituted position is specifically catalyzed by CYP3A of a cytochrome P450 isozyme family in hepatocytes to form a hydroxyl group, and then the resulting product undergoes a ring-opening reaction to form a negatively-charged phosphate intermediate, which has difficulty in passing through the cell membrane and thus exists in the cell. The phosphate intermediate is subjected to hydrolysis and β-elimination reaction, in the presence of phosphodiesterase as a catalyst, to form a nucleoside monophosphate analog, which is further catalyzed by a nucleotide kinase to produce a bioactive nucleotide triphosphate analog. At the same time, aryl vinyl ketone which is a metabolic by-product can be eliminated by 1,4-addition reaction with glutathione, which is abundant in hepatocytes and can resist oxidation and free radicals. The resulting additive product has not been reported to have side effects.

Currently, no monophosphate prodrugs for entecavir are used clinically with high activity, high delivery specificity to the liver, and low toxic and side effects. Therefore, there is an urgent need in the art to develop a novel entecavir prodrug with the advantages such as high activity, high delivery specificity to the liver, and low toxicity and side effects.

SUMMARY

In the present disclosure, a cyclic monophosphate of antiviral entecavir is synthesized and then further modified at its aromatic ring substituent to obtain a class of prodrugs, which are more specifically deliverable to the liver, with higher efficacy and less toxic and side effects.

A first aspect of the present disclosure discloses a compound represented by the following formula I, or an optical isomer, pharmaceutically acceptable salt, hydrate or solvate thereof:

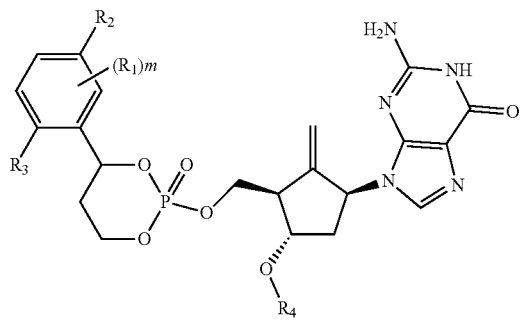

wherein

R1 is each independently selected from halogen, nitro, hydroxyl, amino, cyano, substituted or unsubstituted C1-C6 alkyl, substituted or unsubstituted C3-C8 cycloalkyl, substituted or unsubstituted C1-C6 alkoxy, substituted or unsubstituted C1-C6 alkylamino, substituted or unsubstituted C1-C6 carboxyl, a substituted or unsubstituted C1-C6 ester group, substituted or unsubstituted C2-C6 alkanoyl, and substituted or unsubstituted C2-C6 alkylamido, wherein the substitution involves one or more substituents selected from the group consisting of halogen, C1-C3 alkyl, C1-C3 haloalkyl, nitro, hydroxyl, amino, and cyano;

each of R2 and R3 is independently halogen (For Cl);

m is 0, 1, 2, or 3;

R4 is selected from hydrogen, substituted or unsubstituted C1-C6 alkyl, substituted or unsubstituted C3-C8 cycloalkyl, a substituted or unsubstituted C1-C6 ester group, and substituted or unsubstituted C2-C6 alkanoyl, wherein the substitution involves one or more substituents selected from the group consisting of halogen, C1-C3 alkyl. C1-C3 haloalkyl, nitro, hydroxyl, amino, and cyano; and each chiral center other than the pre-existing chirality in formula I is present in R-configuration or S-configuration.

In an embodiment, R2 is Cl and R3 is F; R2 is Cl and R3 is Cl; or R2 is F and R3 is Cl.

In an embodiment, the optical isomer includes a tautomer a cis- or trans-isomer, a conformer, a meso compound, and an optical isomer having an enantiomeric or diastereomeric relationship.

In an embodiment, the compound is selected from the group consisting of:

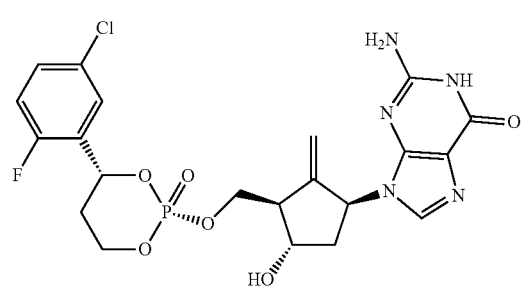

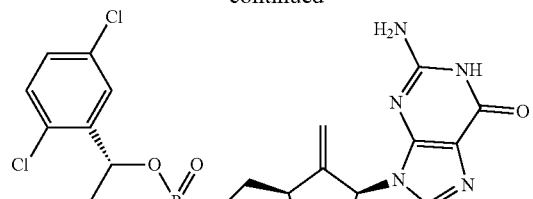

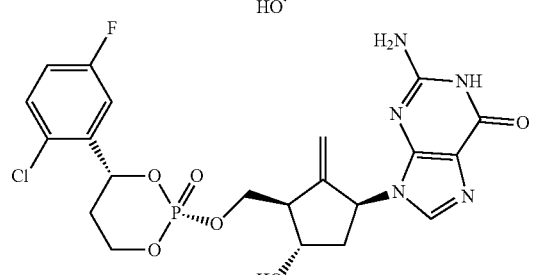

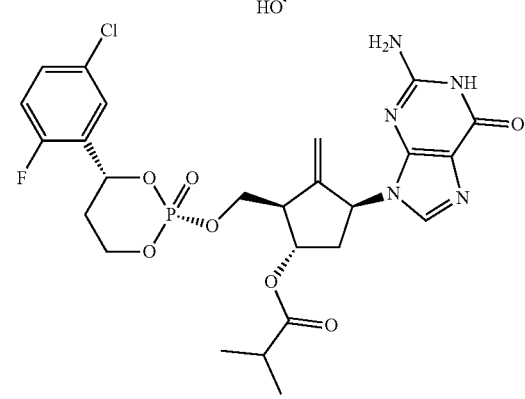

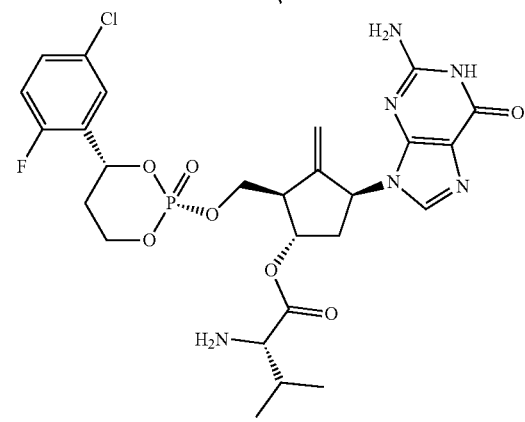

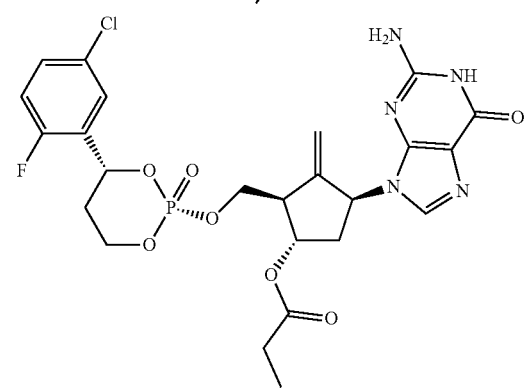

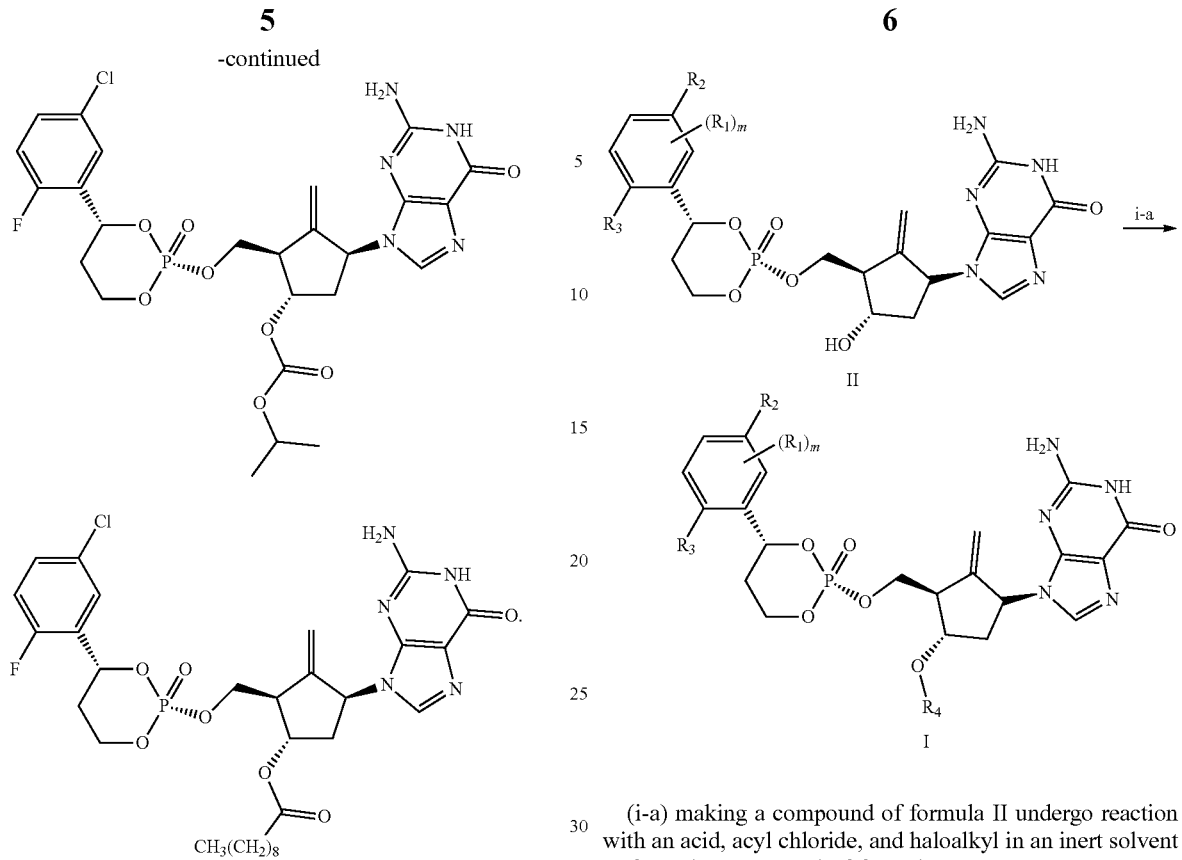

In an embodiment, a salt of the compound represented by formula I is a pharmaceutically acceptable salt formed from the compound represented by formula I and an inorganic acid or an organic acid, or the salt of the compound represented by formula I is a pharmaceutically acceptable salt formed by reaction of the compound represented by formula I with a base. The compound represented by formula I or the salt thereof is amorphous or crystalline.

A second aspect of the present disclosure provides a pharmaceutical composition, comprising: a therapeutically effective amount of a compound, or an optical isomer, pharmaceutically acceptable salt, hydrate or solvate thereof according to the first aspect of the present disclosure; and a pharmaceutically acceptable adjuvant, diluent, or carrier.

A third aspect of the present disclosure provides use of a compound, or an optical isomer, pharmaceutically acceptable salt, hydrate or solvate thereof according to the first aspect of the present disclosure, in the preparation of a pharmaceutical composition for treating and/or preventing an acute or chronic disease associated with hepatitis B virus (HBV) infection.

A fourth aspect of the present disclosure provides a method for preparing the compound of formula I according to the first aspect of the present disclosure, the method comprising a step of:

(i-a) making a compound of formula II undergo reaction with an acid, acyl chloride, and haloalkyl in an inert solvent to form the compound of formula I;

wherein each group in the formula is defined as above.

In an embodiment, in the step (i-a), the reagent is selected from the group consisting of dicyclohexylcarbodiimide (DCC), triethylamine, N,N-diisopropylethylamine, or a combination thereof, wherein DCC and triethylamine are preferred.

In an embodiment, in the step (i-a), the inert solvent is selected from the group consisting of N,N-dimethylformamide, dichloromethane, tetrahydrofuran, or a combination thereof, wherein N,N-dimethylformamide and dichloromethane are preferred as the solvent.

In an embodiment, the reaction in the step (i-a) is carried out at a temperature of 0 to 100° C. (preferably about 25±5° C.).

In an embodiment, the deprotection reaction in the step (i-a) is carried out for a period of 0.5 to 24 hours, preferably 0.5 to 8 hours.

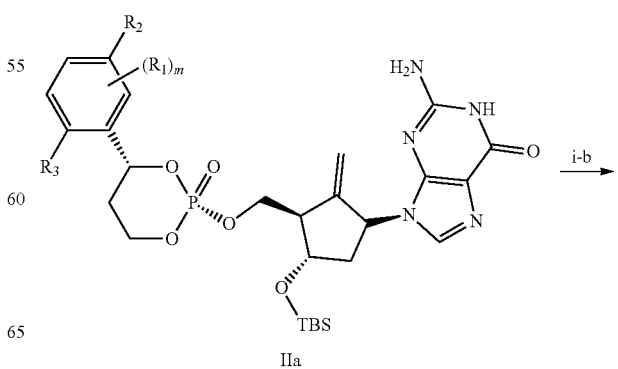

-continued

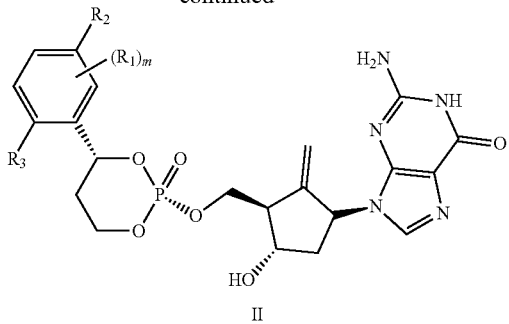

II (i-b) removing TBS from a compound of formula IIa in an inert solvent to form the compound of formula II.

In an embodiment, in the step (i-b), the TBS removing reagent is selected from the group consisting of TBAF, glacial acetic acid, dilute hydrochloric acid, or a combination thereof, wherein a hydrochloric acid-ethanol solution and TBAF are preferred.

In an embodiment, in the step (i-b), the inert solvent is selected from the group consisting of N,N-dimethylformamide, tetrahydrofuran, or a combination thereof, wherein tetrahydrofuran is preferred as the solvent.

In an embodiment, the reaction in the step (i-b) is carried out at a temperature of −50 to 30° C. (preferably about 25±5° C.).

In an embodiment, the deprotection reaction in the step (i-b) is carried out for a period of 0.5 to 6 hours, preferably 0.5 to 3 hours, and more preferably 0.5 to 2 hours.

In an embodiment, the compound of formula IIa is prepared by a method of:

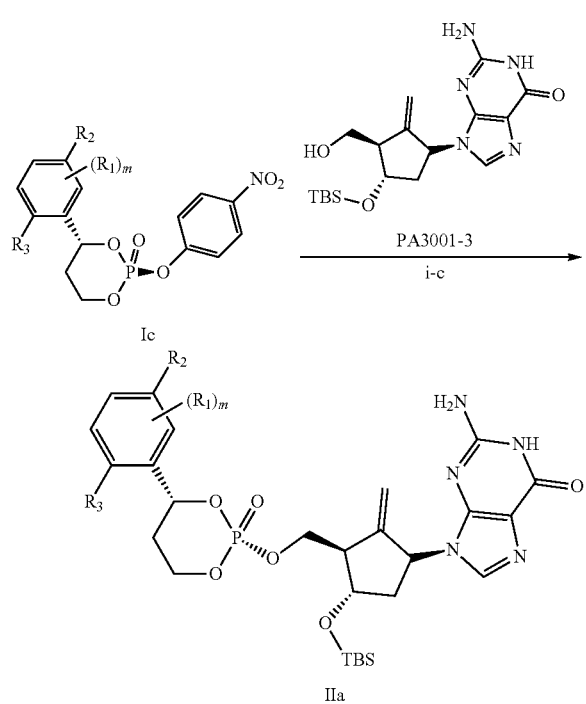

(i-c) making a compound of formula Ic and PA3001-3 undergo a substitution reaction in an inert solvent to obtain the compound of formula IIa.

In an embodiment, in the step (i-c), the reaction is carried out in the presence of a Grignard reagent; and preferably, the Grignard reagent is selected from the group consisting of tert-butylmagnesium chloride (t-BuMgCl).

In an embodiment, the substitution reaction in the step (i-c) is carried out at −50 to 30° C. (preferably about 25±5° C.).

In an embodiment, the substitution reaction in the step (i-c) is carried out for a period of 1 to 72 hours, preferably 3 to 48 hours, and more preferably 6 to 24 hours.

In an embodiment, the inert solvent in the step (i-c) is selected from the group consisting of N,N-dimethylformamide, tetrahydrofuran, or a combination thereof, wherein tetrahydrofuran is preferred as the solvent.

It should be understood that the above various technical features of the present disclosure and various technical features specifically described hereinafter (for example, in embodiments) may be combined with each other, within the scope of the present disclosure, to constitute new or preferred technical solutions, which will not be described in detail here due to the limited number of pages of the specification.

NOTES

Figure 1:
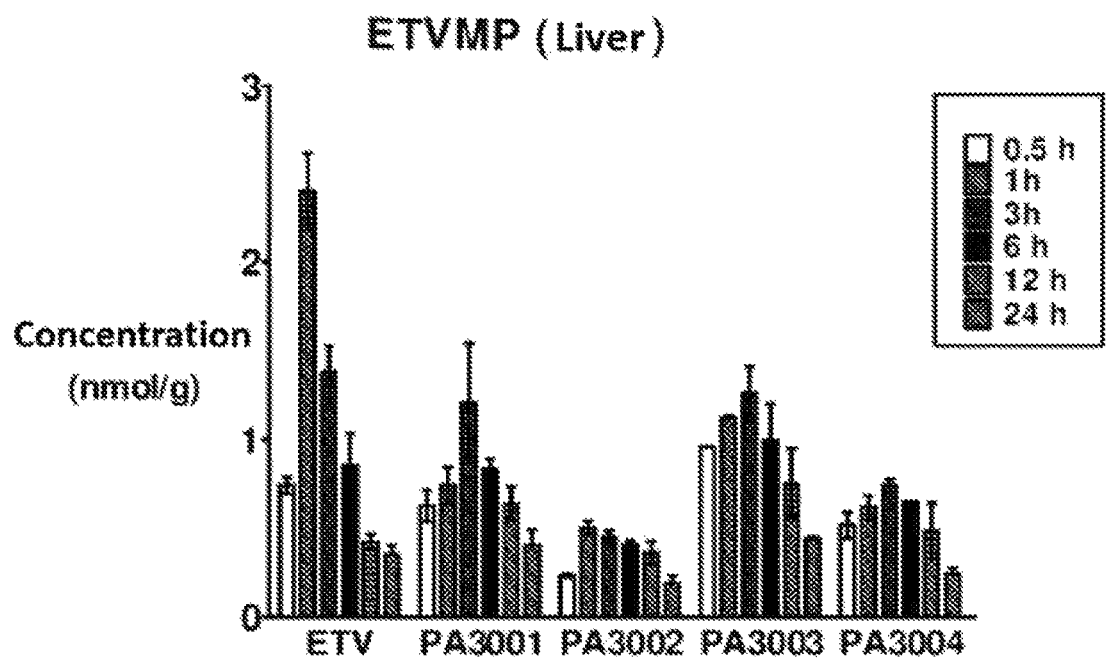
FIG. 1 is a bar chart showing concentrations (nmol/g, molar concentration/tissue weight) of active monophosphate molecules ETVMP in the liver over time after intragastric administration of 0.036 mmol/kg of PA3001, PA3002, PA3003, PA3004, PA3017, and entecavir to rats.

ETV: Entecavir,
2-amino-9-[(1S,3S,4S)-4-hydroxy-3-hydroxymethyl-2-methylenecyclopentyl]-1,9-dihydro-6H-purine-6-one (CAS No: 142217-69-4)
ETVMP:2-amino-9-((1S,3R,4S)-4-hydroxy-3-(monophosphate methylene)-2-methylenecyclopentyl)-3H-purine-6 (9H)-one (CAS No: 1103994-53-1)

DETAILED DESCRIPTION OF EMBODIMENTS

Through a long-term and in-depth research, the inventors have first found, after the screening and researching of a large number of compounds, that a class of compounds of formula I and formula II having specific structures (with specific halogens at sites 2 and 5 of the benzene ring moiety) have surprisingly excellent antiviral activity, significantly improved delivery specificity to the liver and significantly reduced toxic and side effects. The present disclosure is accomplished by the inventors based on the above discovery.

TERMINOLOGY

As used herein, the term "C1-C6 alkyl" refers to a straight or branched chain alkyl having 1 to 6 carbon atoms, such as methyl, ethyl, propyl, isopropyl, butyl, isobutyl, sec-butyl, tert-butyl, or similar groups.

As used herein, the term "C2-C6 alkanoyl" refers to a substituent having a structure of a "straight or branched chain alkyl-carbonyl having 1-6 carbon atoms", such as acetyl, propionyl, butyryl, or similar groups.

As used herein, the term "C1-C6 alkylamino" refers to a substituent having a structure of a "straight or branched chain alkyl-amino having 1-6 carbon atoms", such as methylamino, dimethylamino, ethylamino, propylamino, diethylamino, or similar groups.

The term "halogen" refers to F, C1, Br, or I.

In the present disclosure, the term "containing", "including", or "comprising" means that various ingredients may be employed together in the mixture or composition of the present disclosure. Therefore, the terms "consisting essentially of" and "consisting of" are included in the term "containing".

In the present disclosure, the term "pharmaceutically acceptable" ingredient refers to a substance that is suitable for humans and/or animals without undue adverse side effects (such as toxicity, irritation, and allergic response) commensurate with a reasonable benefit/risk ratio.

In the present disclosure, the term "effective amount" refers to an amount of a therapeutic agent to treat, alleviate, or prevent a target disease or condition, or an amount of a therapeutic agent to yield a detectable therapeutic or prophylactic effect. An exact effective amount for a certain subject depends on the body size and health condition of the subject, the nature and extent of the disorder, and the therapeutic agent and/or a combination of therapeutic agents selected for administration. Therefore, it is useless to specify an exact effective amount in advance. However, the amount effective for a given condition can be determined by a clinician through routine experimentation.

Herein, the term "substitution", unless otherwise specified, means that one or more hydrogen atoms on a group are substituted with a substituent selected from the group consisting of halogen, C1-C3 alkyl, C1-C3 haloalkyl, nitro, hydroxyl, amino, and cyano.

Unless otherwise specified, all compounds involved in the present disclosure are intended to include all possible optical isomers, such as single chiral compounds, or a mixture of various different chiral compounds (i.e., racemate). In all the compounds of the present disclosure, each of the chiral carbon atoms may optionally be present in R-configuration or S-configuration, or in a mixture of R-configuration and S-configuration.

As used herein, the term "compound of the present disclosure" refers to a compounds represented by formula I and formula II. Such term further involves various crystal forms, pharmaceutically acceptable salts, hydrates or solvates of the compound of formula I and formula II.

As used herein, the term "pharmaceutically acceptable salt" refers to a salt formed from the compound of the present disclosure and an acid or base and suitable for use as a medicament. The pharmaceutically acceptable salts include inorganic salts and organic salts. A preferred class of salts are formed from the compounds of the present disclosure and an acid. The acids suitable for forming the salts include but are not limited to: inorganic acids such as hydrochloric acid, hydrobromic acid, hydrofluoric acid, sulfuric acid, nitric acid and phosphoric acid, organic acids such as formic acid, acetic acid, propionic acid, oxalic acid, malonic acid, succinic acid, fumaric acid, maleic acid, lactic acid, malic acid, tartaric acid, citric acid, picric acid, methanesulfonic acid, phenylmethanesulfonic acid and benzenesulfonic acid, and acidic amino acids such as aspartic acid and glutamic acid.

Some of the compounds of the present disclosure may be crystallized or recrystallized with water or various organic solvents, in which case various solvates may be formed. The solvates of the present disclosure include stoichiometric solvates such as hydrates, and also include compounds formed when prepared by the low pressure sublimation drying method and containing a variable amount of water.

It should be understood that various thermodynamically stable isomers, such as tautomers, conformers, meso compounds, and optical isomers having enantiomeric or diastereomeric relationship, may be present after preparation of the compounds of the present disclosure. Such variant forms will be apparent to those skilled in the art after reading the content of the present disclosure.

Compound of Formula I and Preparation Thereof

In order to provide a highly effective and low toxic prodrug for liver specific delivery which enables a concentrated release of an antiviral nucleotide drug in hepatocytes through a liver specific delivery mechanism, the inventors have prepared a compound of formula I:

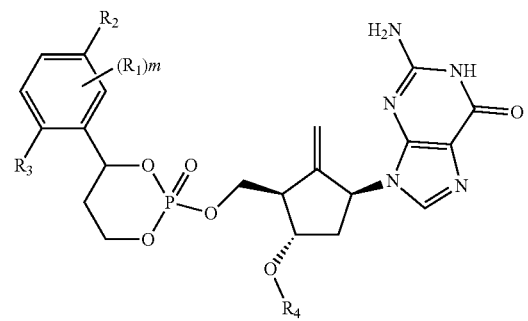

wherein

R1 is each independently selected from halogen, nitro, hydroxyl, amino, cyano, substituted or unsubstituted C1-C6 alkyl, substituted or unsubstituted C3-C8 cycloalkyl, substituted or unsubstituted C1-C6 alkoxy, substituted or unsubstituted C1-C6 alkylamino, substituted or unsubstituted C1-C6 carboxyl, a substituted or unsubstituted C1-C6 ester group, substituted or unsubstituted C2-C6 alkanoyl, and substituted or unsubstituted C2-C6 alkylamido, wherein the substitution involves one or more substituents selected from the group consisting of halogen, C1-C3 alkyl, C1-C3 haloalkyl, nitro, hydroxyl, amino, and cyano;

m is 0, 1, 2, or 3;

each of R2 and R3 is independently halogen (F or C1);

R4 is independently selected from hydrogen, substituted or unsubstituted C1-C6 alkyl, substituted or unsubstituted C3-C8 cycloalkyl, a substituted or unsubstituted C1-C6 ester group, and substituted or unsubstituted C2-C6 alkanoyl, wherein the substitution involves one or more substituents selected from the group consisting of halogen, C1-C3 alkyl, C1-C3 haloalkyl, nitro, hydroxyl, amino, and cyano; and each chiral center other than the pre-existing chirality in formula I is present in R-configuration or S-configuration.

The compound may be a racemate or an optical isomer, both of which have certain antiviral activity. The preferred compound of formula I has a structure selected from the group consisting of:

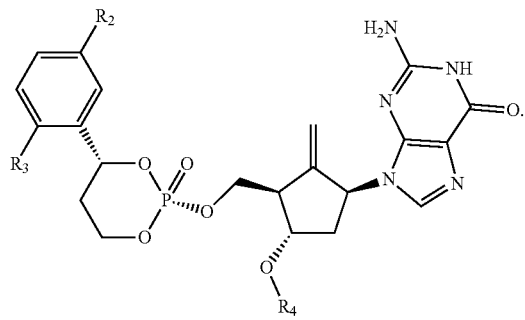

In an embodiment, the P2 and the aromatic group at the site 4 in the phosphate ring structure are cis to each other, and P2 is in R-configuration, and C4 is in S-configuration.

In an embodiment, R2 is Cl and R3 is F; R2 is Cl and R3 is Cl; or R2 is F and R3 is Cl.

In an embodiment, the optical isomer includes a tautomer, a cis- or trans-isomer, a conformer, a meso compound, and an optical isomer having an enantiomeric or diastereomeric relationship.

In an embodiment, the compound is selected from the group consisting of:

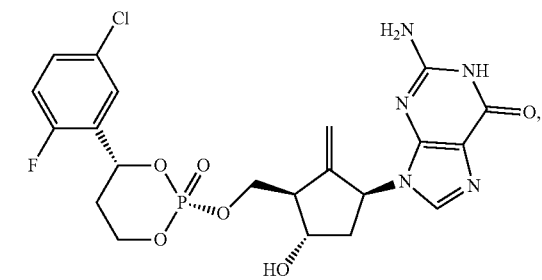

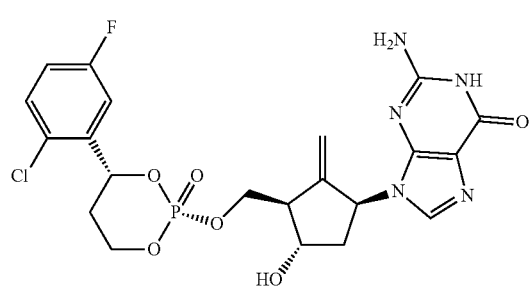

or

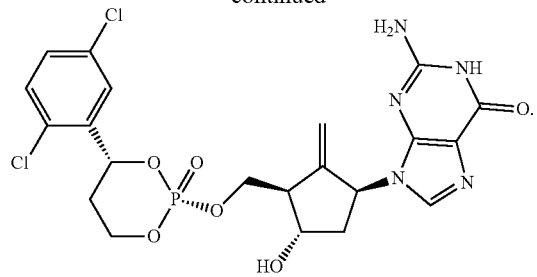

The Compound of General Formula I is Prepared by the Following Method:

A compound PA3001-3 is added to a tetrahydrofuran solution, and then tert-butylmagnesium chloride is added dropwise at 0° C., and a reaction is carried out for 30 min. Then, a compound Ic is added one time. The reaction is carried out overnight and quenched. The resulting product is purified by silica gel column chromatography to obtain an intermediate IIa. The intermediate IIa is added to a hydrochloric acid-ethanol solution so that the protecting group TBS is removed to obtain a compound of general formula II. The compound of formula II is reacted with an acid, acyl chloride, and haloalkyl to give the compound of general formula I.

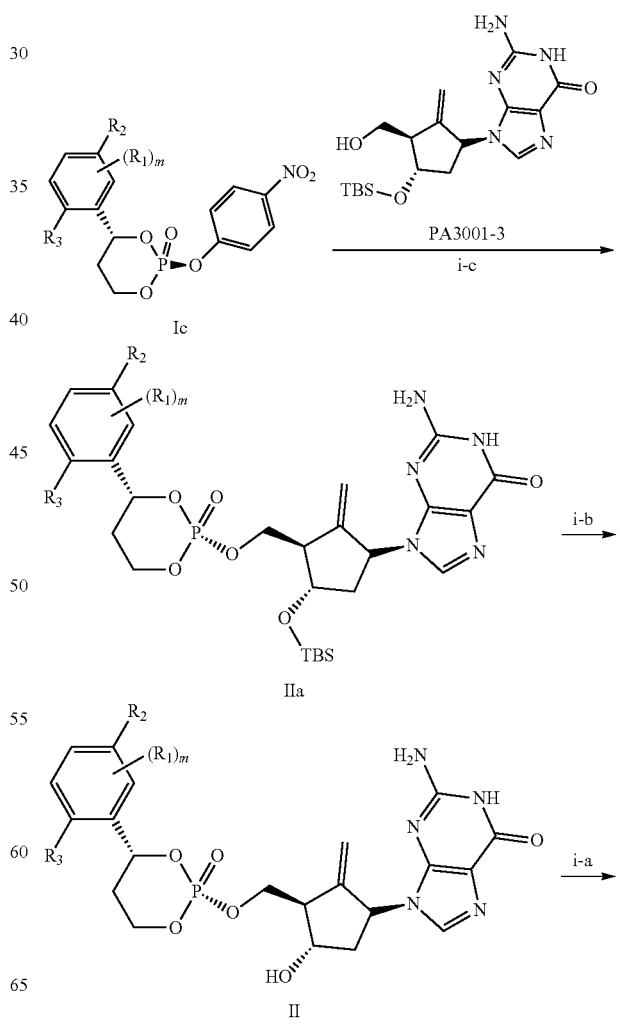

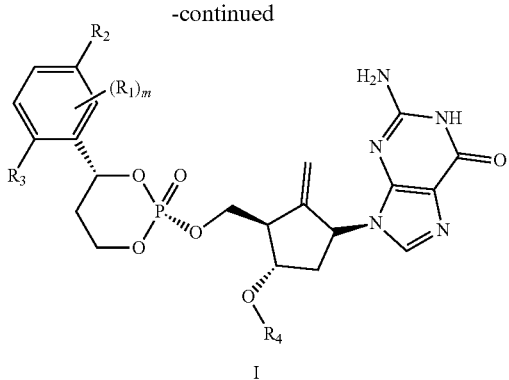

I

Herein, each of the reactants may be commercially available or may be prepared by a conventional method in the art using commercially available raw materials.

Pharmaceutical Composition and Administration Method

Since the compound of the present disclosure has an excellent inhibitory activity against hepatitis B virus, the compound of the present disclosure and various crystal forms, pharmaceutically acceptable inorganic or organic salts, hydrates or solvates thereof, and a pharmaceutical composition containing the compound of the present disclosure acting as a main active ingredient can be used for the treatment, prevention, and alleviation of diseases caused by hepatitis B virus. According to the prior art, the compound of the present disclosure can be used for treatment of diseases caused by infections with HBV, HCV, HIV, HCMV, and the like.

The pharmaceutical composition of the present disclosure comprises a safe and effective amount of the compound of the present disclosure or a pharmacologically acceptable salt thereof, and a pharmacologically acceptable excipient or carrier. Here, the "safe and effective amount" refers to an amount of the compound sufficient to significantly ameliorate symptoms without causing serious side effects. Generally, the pharmaceutical composition comprises the compound of the present disclosure at 0.1 to 1000 mg per dose, and preferably at 0.5 to 500 mg per dose. Preferably, the "per dose" refers to one capsule or tablet.

The "pharmaceutically acceptable carrier" refers to one or more compatible solid or liquid fillers or gel materials, which are suitable for use in humans and must have sufficient purity and sufficiently low toxicity. The term "compatible" indicates herein that the various components of a composition can be blended with each other and with the compound of the present disclosure without significantly reducing the efficacy of the compound. Some examples of the pharmaceutically acceptable carriers include cellulose and its derivatives (such as sodium carboxymethylcellulose, sodium ethylcellulose, and cellulose acetate), gelatin, talc, solid lubricants (such as stearic acid, and magnesium stearate), calcium sulfate, vegetable oils (such as soybean oil, sesame oil, peanut oil, and olive oil), polyols (such as propylene glycol, glycerin, mannitol, and sorbitol), emulsifiers (such as Tween@), wetting agents (such as lauryl sodium sulfate), colorants, flavoring agents, stabilizers, antioxidants, preservatives, pyrogen-free water, and the like.

The administration forms of the compound or the pharmaceutical composition of the present disclosure are not particularly limited, and representative administration forms include but are not limited to: oral, rectal, parenteral (intravenous, intramuscular, or subcutaneous), and topical administrations. Oral administration is a particularly preferable administration form.

Solid dosage forms used for oral administration include capsule, tablet, pill, powder, and granule. In such solid dosage forms, the active compound is mixed with at least one conventional inert excipient (or carrier), such as sodium citrate or dicalcium phosphate, or mixed with the following components including: (a) a filler or compatibilizer, such as starch, lactose, sucrose, glucose, mannitol and silicic acid; (b) a binder, such as hydroxymethylcellulose, alginate, gelatin, polyvinylpyrrolidone, sucrose and Arabic gum; (c) a humectant, such as glycerin; (d) a disintegrating agent, such as agar, calcium carbonate, potato starch or tapioca starch, alginic acid, some composite silicates and sodium carbonate; (e) a slow solvent, such as paraffin; (f) an absorbing accelerator, such as quaternary amine compounds; (g) a wetting agent, such as cetanol and glyceryl monostearate; (h) an adsorbent, such as kaoline; and (i) a lubricant, such as talc, calcium stearate, magnesium stearate, solid polyethylene glycol, lauryl sodium sulfate, or a mixture thereof. A buffering agent may also be comprised in the dosage forms of capsule, tablet, and pill.

Solid dosage forms such as tablet, sugar pill, capsule, pill, and granule may be prepared using coatings or shell materials, such as enteric coatings and other materials well known in the art. They may comprise an opacifying agent, and the active compound or compound of the composition may be released in a certain part of the digestive tract in a delayed manner. Examples of usable embedding components include polymeric substances and waxy substances. If necessary, a microcapsule may be formed from the active compound and one or more of the above-mentioned excipients.

Liquid dosage forms used for oral administration include pharmaceutically acceptable emulsion, solution, suspension, syrup, or tincture. The liquid dosage forms may comprise, in addition to the active compounds, inert diluents conventionally used in the art, such as water or other solvents, solubilizers and emulsifiers, including ethanol, isopropanol, ethyl carbonate, ethyl acetate, propylene glycol, 1,3-butanediol, dimethylformamide and oils, especially cottonseed oil, peanut oil, corn germ oil, olive oil, castor oil and sesame oil, or a mixture thereof.

In addition to such inert diluents, the composition may also comprise adjuvants, such as wetting agents, emulsifiers, suspending agents, sweeteners, corrigents, and fragrances.

In addition to the active compound, the suspension may comprise a suspending agent, such as ethoxylated isooctadecanol, polyoxyethylene sorbitol and sorbitan ester, microcrystalline cellulose, aluminum methoxide and agar, and a mixture thereof.

The composition used for parenteral injection may comprise a physiologically acceptable sterile aqueous or non-aqueous solution, dispersion liquid, suspension or emulsion, and sterile powder for redissolution into a sterile injectable solution or dispersion liquid. Appropriate aqueous and non-aqueous carriers, diluents, solvents or excipients include water, ethanol, polyols, and an appropriate mixture thereof.

Dosage forms of the compounds of the present disclosure used for topical administration include ointment, powder, patch, spraying agent, and inhalant. The active ingredients are mixed together, under a sterile condition, with physiologically acceptable carriers and any preservatives or buffering agents, or propellants which may be required if necessary.

The compound of the present disclosure may be administered alone or in combination with other pharmaceutically acceptable compounds.

When the pharmaceutical composition is used, a safe and effective amount of the compound of the present disclosure is administered to a mammal (such as a human) in need thereof, wherein a pharmaceutically acceptable effective dosage is administered. For a person of 60 kg body weight, the compound is administered at a daily dosage of usually 0.2 to 1,000 mg, and preferably 0.5 to 100 mg. Certainly, other factors including administration routes and health conditions of patients should also be taken into consideration for determining specific dosages, which is within the skill range of the skilled physician.

The main advantages of the present disclosure are described as follows:

(1) High Specific Delivery to Liver: the compound can only be catalyzed specifically by CYP3A of the cytochrome P450 isozyme family in hepatocytes to generate active molecules, which are highly negatively charged and are not easily excreted from the liver. There is almost no expression of CYP3A enzyme in other tissues, thus the active molecules are distributed at a much higher concentration in the liver than in other tissues, whereby the liver specific delivery effect is achieved.

(2) High Activity: the compound can only be catalyzed specifically by CYP3A of the cytochrome P450 isozyme family in hepatocytes to generate active molecules, which are highly negatively charged and are not easily excreted from the liver, and the compound orally administered and absorbed is first metabolized by the liver (subjected to the first pass effect), thus more active molecules are accumulated in the liver, and thus the antiviral activity can also be greatly improved.

(3) Low Toxic and Side Effects: the same dosage of prodrugs is rarely metabolized into active molecules in tissues other than the liver, thus their toxicity to major organs such as kidney and brain is greatly reduced.

The present disclosure will be further described below in connection with specific examples. It should be understood that these examples are merely intended to illustrate the disclosure but not intended to limit the scope of the present disclosure. In the following examples, the experimental methods, in which the specific conditions are not specified, are usually carried out according to conventional conditions or the conditions recommended by the manufacturers. Unless otherwise specified, percentages and parts are calculated by weight.

Example 1: PA3001 (Comparative Example)

Synthetic Route:

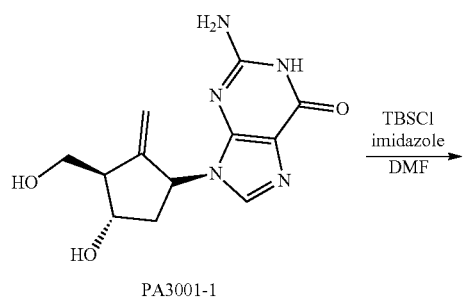

PA3001-1

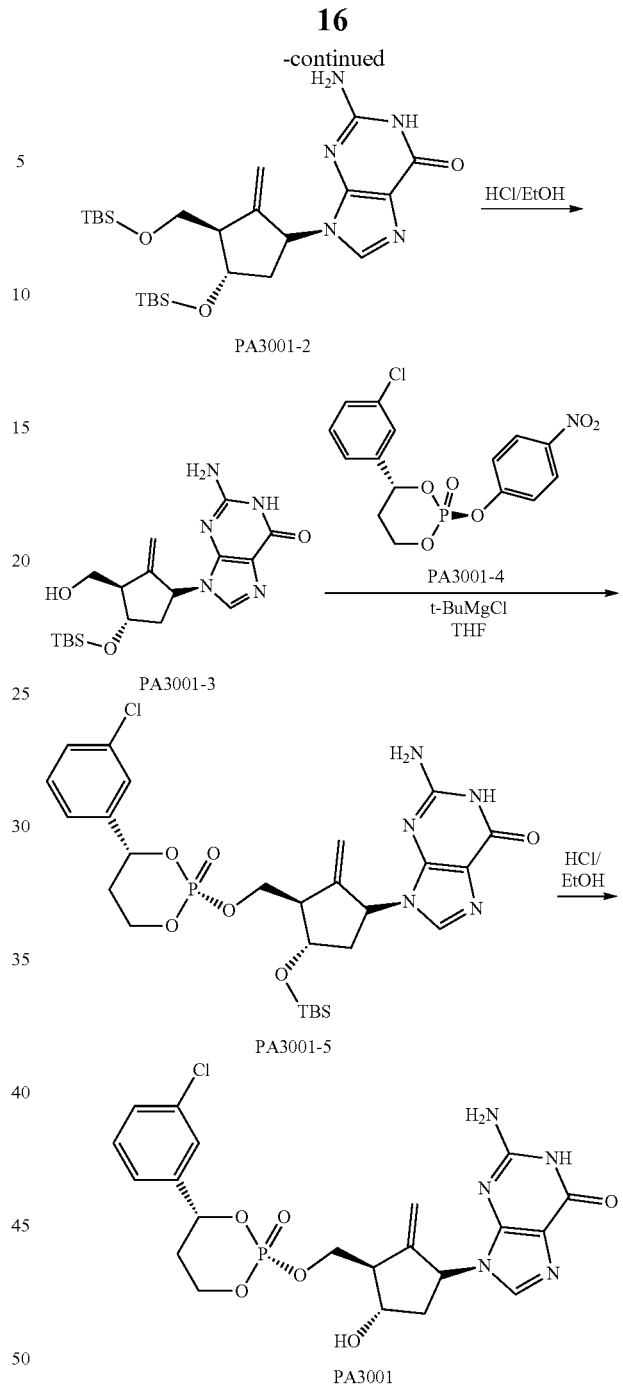

Experimental Section:

Step 1) Synthesis of Compound PA3001-2:

Compound PA3001-1 (i.e., an entecavir monohydrate) (5.32 g, 18 mmol) and imidazole (8.0 g, 117.6 mmol) were dissolved in DMF (40 ml), and tert-butyldimethylchlorosilane (TBSC, 13.3 g, 88 mmol) was slowly added under an ice bath.

The mixture was stirred at room temperature and reacted overnight under the protection of nitrogen. After the reaction was finished, the resulting product was slowly added to water (400 mL), stirred for 15 minutes, extracted with ethyl acetate (3×150 ml), dried over anhydrous sodium sulfate, filtered, and dried by rotary evaporation. The residue was separated and purified by silica gel chromatography column (eluent: PE:EA (V:V)=1:3) to give PA3001-2 (8.2 g) with a yield of 90%.

Step 2) Synthesis of Compound PA3001-3:

The compound PA3001-2 (2.5 g, 4.9 mmol) was dissolved in 0.5% hydrochloric acid-ethanol solution (50 ml), stirred at room temperature for 0.5 hours, and quickly neutralized with a saturated NaHCO₃ solution to pH=9. The ethanol was removed by rotary evaporation. The residue was separated and purified by silica gel chromatography column (eluent: PE:EA:CH3OH (V:V)=30:150:4.5) to give a white solid compound PA3001-3 (1.5 g) with a yield of 78%.

Step 3) Synthesis of Compound PA3001-5:

The compound PA3001-3 (484 mg, 1.24 mmol) was dissolved in anhydrous tetrahydrofuran, to which a 1M tert-butylmagnesium chloride solution (4.9 ML, 4.9 mmol) was slowly added dropwise under an ice bath and stirred for 1 hour. PA3001-4 (633 mg, 1.71 mmol) was added and stirred at room temperature overnight. The reaction was quenched by adding 20 mL of saturated ammonium chloride. The resulting product was extracted with ethyl acetate (3×100 mL), washed with saturated brine, dried over anhydrous sodium sulfate, and dried by rotary evaporation. The residue was separated and purified by silica gel chromatography column (DCM:MeOH (V:V)=20:1) to give PA3001-5 (538 mg) with a yield of 70%.

Step 4) Synthesis of Compound PA3001:

The compound PA3001-5 (270 mg, 0.43 mmol) was added to a 2% hydrochloric acid-ethanol solution (10 mL) and stirred at room temperature for 2 hours. After the reaction was finished, the resulting product was neutralized with a saturated NaHCO₃ solution to a neutral pH value. The ethanol was removed by rotary evaporation, and then the residue was extracted with ethyl acetate (2×50 mL). The organic phase was washed with saturated brine, dried over anhydrous sodium sulfate, filtered, and dried by rotary evaporation. The residue was purified by Combiflash chromatography column to give a pale white solid PA3001 (155 mg) with a yield of 70%.

Example 2: PA3002

Synthetic Route:

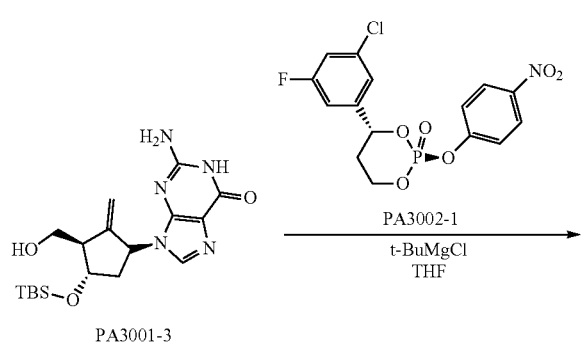

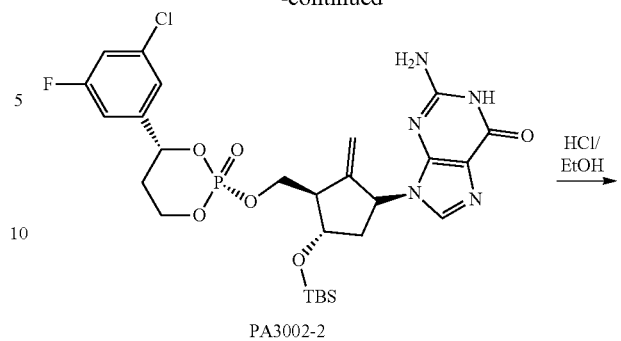

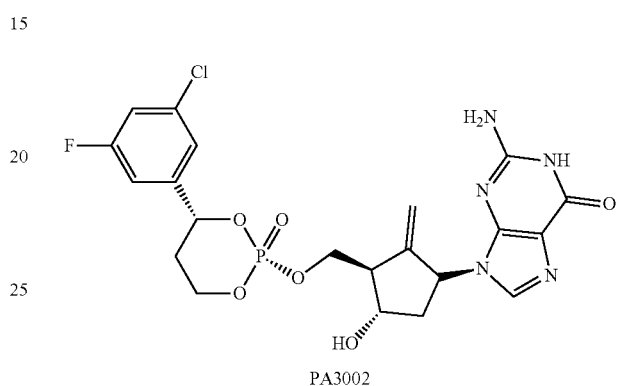

Step 1) Synthesis of Compound PA3002-2:

The compound PA3001-3 (561 mg, 1.4 mmol) was dissolved in tetrahydrofuran (30 ml), to which a 1M tert-butylmagnesium chloride solution (5.6 mL, 5.6 mmol, 4.0 eq) was slowly added dropwise under an ice bath. When the dropwise addition was completed, the reaction solution was stirred at room temperature for 1 hour and then cooled to 0° C. PA3002-1 (833 mg, 2.1 mmol) was added. Then, the reaction solution was stirred at room temperature overnight. The reaction was quenched with a saturated aqueous ammonium chloride solution (30 mL). The resulting product was extracted with ethyl acetate (3×100 mL), dried over anhydrous Na2SO4, filtered, and dried by rotary evaporation. The residue was separated and purified by silica gel chromatography column (eluent: DCM:MeOH (V:V)=20:1) to give a white solid PA3002-2 (600 mg) with a yield of 65%.

Step 2) Synthesis of Target Compound PA3002:

The compound PA3002-2 (310 mg, 0.48 mmol) was dissolved in 3.6% hydrochloric acid-ethanol solution (15 ml), and the mixture was stirred and reacted at room temperature for 2 hours. After the reaction was finished, the resulting product was neutralized with a saturated NaHCO₃ solution to a neutral pH value. The ethanol was removed by rotary evaporation, and then the residue was extracted with ethyl acetate (2×60 mL). The organic phase was washed with saturated brine, dried over anhydrous sodium sulfate, filtered, and dried by rotary evaporation. The residue was purified by Combiflash chromatography column to give a pale white solid PA3002 (170 mg) with a yield of 66%.

19

Example 3: PA3003

Synthetic Route:

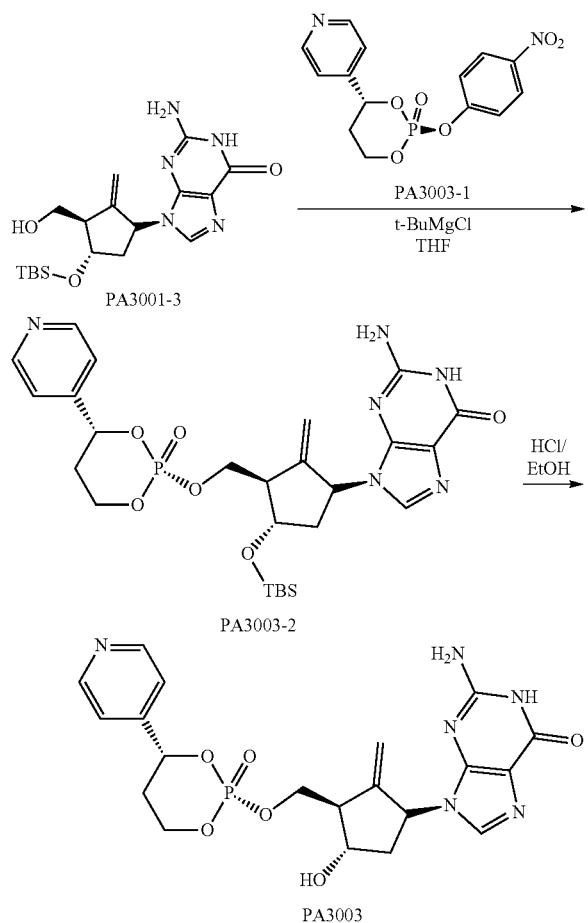

Experimental Section:

Step 1) Synthesis of Compound PA3003-2:

The compound PA3001-3 (900 mg, 2.3 mmol) was dissolved in tetrahydrofuran (50 ml), to which a 1M tert-butylmagnesium chloride solution (4.6 mL, 4.6 mmol) was slowly added dropwise under an ice bath. When the dropwise addition was completed, the reaction solution was stirred at room temperature for 1 hour and then cooled to 0° C. PA3003-1 (1.17 g, 3.5 mmol) was added. Then, the reaction solution was stirred at room temperature overnight. The reaction was quenched with a saturated aqueous ammonium chloride solution (30 mL). The resulting product was extracted with ethyl acetate (3×150 mL), dried over anhydrous Na2SO4, filtered, and dried by rotary evaporation. The residue was separated and purified by silica gel chromatography column (eluent: DCM:MeOH (V:V)=10:1) to give a white solid PA3003-2 (700 mg) with a yield of 64%.

Step 2) Synthesis of Target Compound PA3003:

The compound PA3003-2 (600 mg, 1.02 mmol) was dissolved in 3.6% hydrochloric acid-ethanol solution (15 ml), and the mixture was stirred and reacted at room temperature for 2 hours. After the reaction was finished, the resulting product was neutralized with a saturated NaHCO3 solution to a neutral pH value. The ethanol was removed by rotary evaporation, and then the residue was extracted with ethyl acetate (2×100 mL). The organic phase was washed with saturated brine, dried over anhydrous sodium sulfate, filtered, and dried by rotary evaporation. The residue was purified by Combiflash chromatography column to give a pale white solid PA3003 (200 mg) with a yield of 41%.

Example 4: PA3004

Synthetic Route:

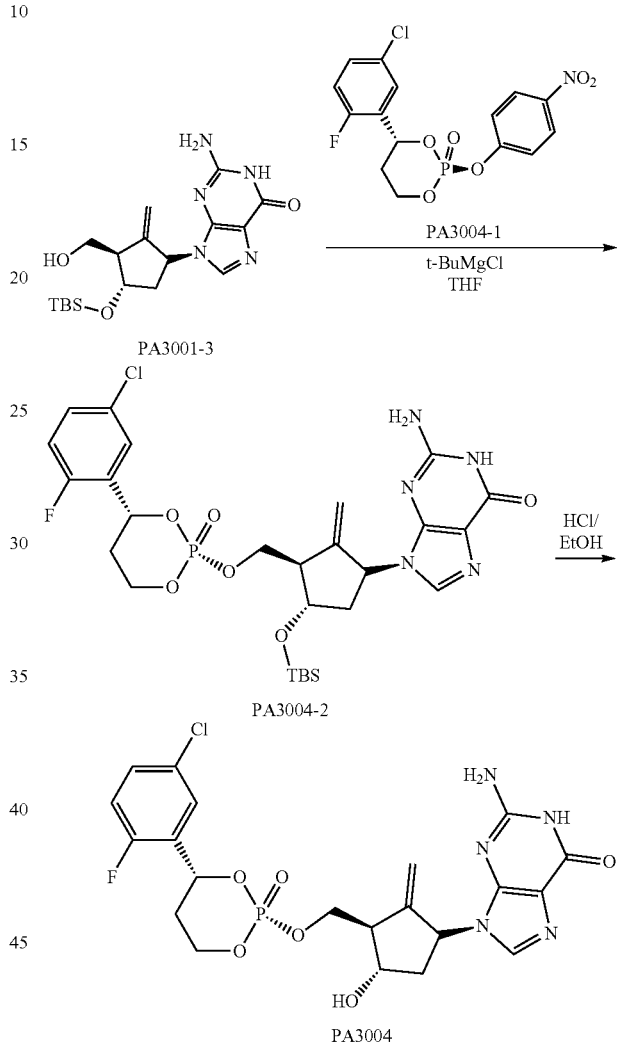

Experimental Section:

Step 1) Synthesis of Compound PA3004-2:

The compound PA3001-3 (677 mg, 1.73 mmol) was dissolved in tetrahydrofuran (40 ml), to which a 1M tert-butylmagnesium chloride solution (6.6 mL, 6.6 mmol) was slowly added dropwise under an ice bath. When the dropwise addition was completed, the reaction solution was stirred at room temperature for 1 hour and then cooled to 0° C. PA3004-1 (970 mg, 2.5 mmol) was added. Then, the reaction solution was stirred at room temperature overnight. The reaction was quenched with a saturated aqueous ammonium chloride solution (30 mL). The resulting product was extracted with ethyl acetate (3×150 mL), dried over anhydrous Na2SO4, filtered, and dried by rotary evaporation. The residue was separated and purified by silica gel chromatography column (eluent: DCM:MeOH (V:V)=20:1) to give a white solid PA3004-2 (580 mg) with a yield of 53%.

Step 2) Synthesis of Target Compound PA3004:

The compound PA3004-2 (580 mg, 0.91 mmol) was dissolved in 3.6% hydrochloric acid-ethanol solution (15 ml), and the mixture was stirred and reacted at room temperature for 2 hours. After the reaction was finished, the resulting product was neutralized with a saturated NaHCO₃ solution to a neutral pH value. The ethanol was removed by rotary evaporation, and then the residue was extracted with ethyl acetate (2×80 mL). The organic phase was washed with saturated brine, dried over anhydrous sodium sulfate, filtered, and dried by rotary evaporation. The residue was purified by Combiflash chromatography column to give a pale white solid PA3004 (250 mg) with a yield of 52%.

Example 5: PA3005

Synthetic Route:

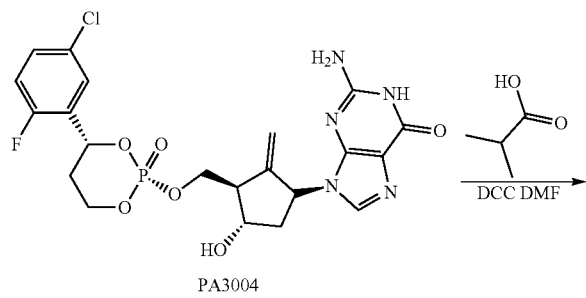

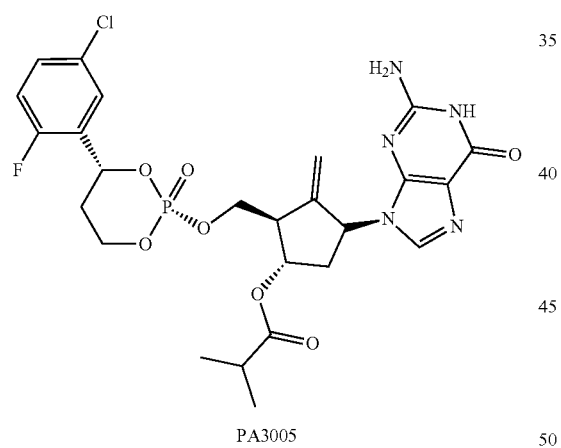

Experimental Section:

Step 1) Synthesis of Compound PA3005:

The compound PA3004 (300 mg, 0.57 mmol) was dissolved in DMF (10 ml), to which DCC (352 mg, 1.71 mmol), isobutyric acid (60 mg, 0.68 mmol), and a catalytic amount of DMAP (10 mg) were added at room temperature. Then, the reaction solution was stirred at room temperature overnight. The reaction was quenched with a saturated aqueous sodium chloride solution (40 mL). The resulting product was extracted with ethyl acetate (3×50 mL), dried over anhydrous Na2SO4, filtered, and dried by rotary evaporation. The residue was purified by Combiflash chromatography column to give a white solid PA3005 (206 mg) with a yield of 61%.

Example 6: PA3006

Synthetic Route:

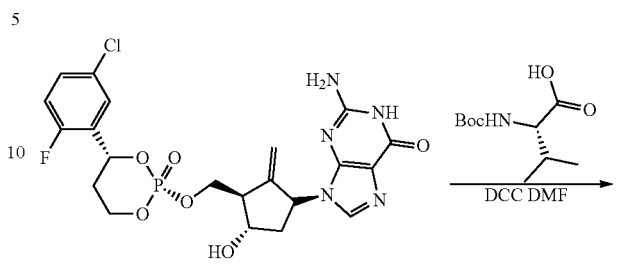

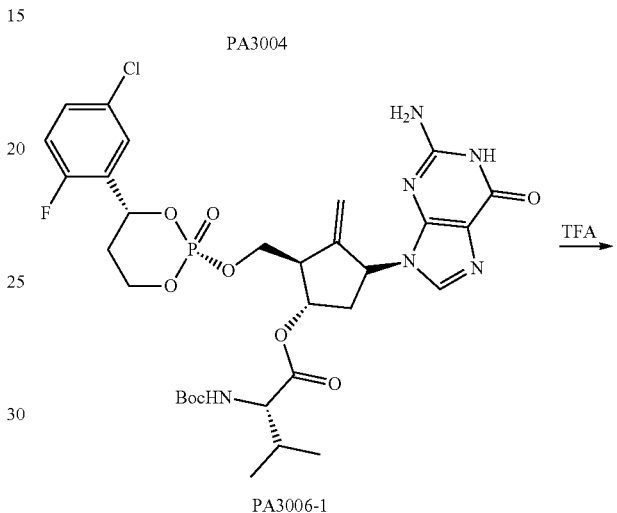

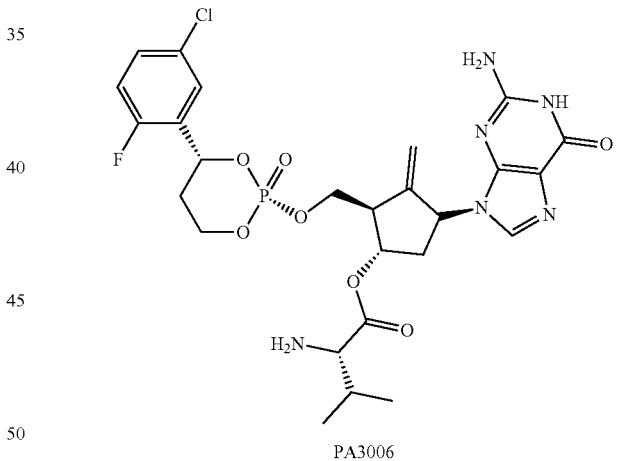

Experimental Section:

Step 1) Synthesis of Compound PA3006-1:

The compound PA3004 (200 mg, 0.38 mmol) was dissolved in DMF (10 ml). DCC (234 mg, 1.14 mmol), (S)-2-((tert-butoxycarbonyl)amino)-3-methylbutyric acid (124 mg, 0.68 mmol), and a catalytic amount of DMAP (10 mg) were added at room temperature. Then, the reaction solution was stirred at room temperature overnight. The reaction was quenched with a saturated aqueous sodium chloride solution (40 mL). The resulting product was extracted with ethyl acetate (3×50 mL), dried over anhydrous Na2SO4, filtered, and dried by rotary evaporation. The residue was purified by Combiflash chromatography column to give a white solid PA3006-1 (180 mg) with a yield of 65%.

Step 2) Synthesis of Compound PA3006:

The compound PA3006-1 (180 mg, 0.25 mmol) was dissolved in a trifluoroacetic acid solution (5 ml), and the mixture was stirred and reacted at room temperature for 2 hours. After the reaction was finished, trifluoroacetic acid was removed by rotary evaporation and then the residue was dissolved in 40 mL of ethyl acetate, to which 50 mL of water was added. The mixture was neutralized with a saturated NaHCO₃ solution to a neutral pH value. The organic phase was washed with saturated brine, dried over anhydrous sodium sulfate, filtered, and dried by rotary evaporation. The residue was purified by Combiflash chromatography column to give a pale white solid PA3006 (78 mg) with a yield of 50%.

Example 7: PA3007

Synthetic Route:

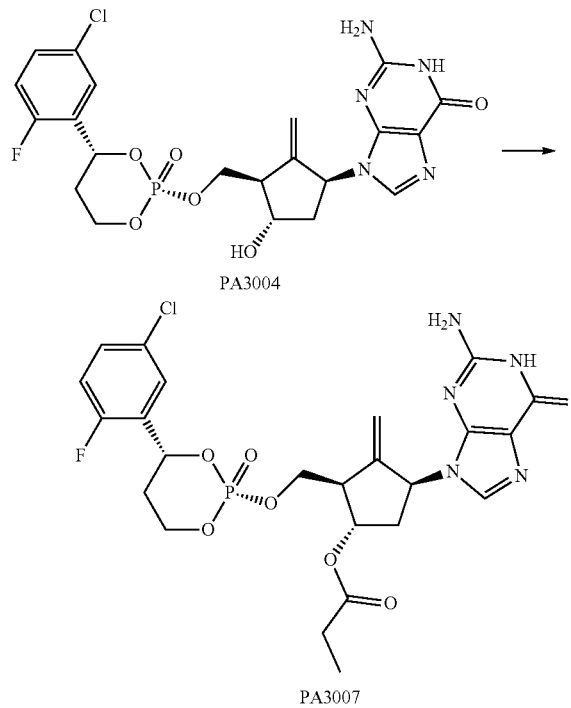

Experimental Section:

Step 1) The compound PA3004 (200 mg, 0.38 mmol), DCC (235 mg, 1.14 mmol), and DMAP (5 mg, 0.038 mmol) were dissolved in a mixed solvent of N,N-dimethylformamide and dichloromethane (V:V=1:1, 10 ml), to which propionic acid (45 µL, 0.76 mmol) was slowly added dropwise under an ice bath. When the dropwise addition was completed, the reaction solution was stirred at room temperature overnight.

After the reaction solution was concentrated, a saturated aqueous sodium chloride solution (10 mL) was added. The reaction solution was extracted with ethyl acetate (3×30 mL), dried over anhydrous Na2SO4, filtered, and dried by rotary evaporation. The residue was separated and purified by silica gel chromatography column (eluent: DCM:MeOH (V:V) 20:1) to give a white solid PA3007 (105 mg) with a yield of 47%.

Example 8: PA3008

Synthetic Route:

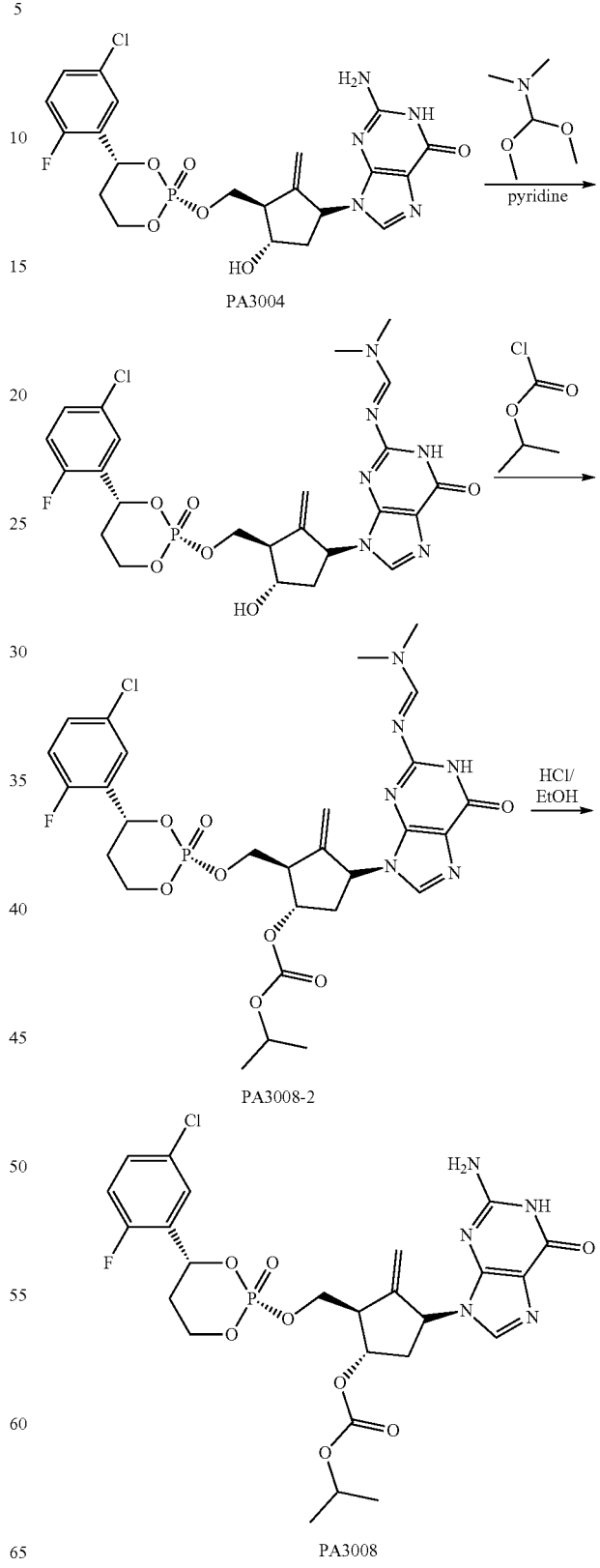

Experimental Section:

Step 1) Synthesis of Compound PA3008-1:

The compound PA3004 (500 mg, 0.95 mmol) was dissolved in pyridine (5 mL), to which N,N-dimethylforaidedimethyl acetal (0.2 mL, 1.9 mmol) was slowly added dropwise under an ice bath. When the dropwise addition was completed, the reaction solution was stirred at room temperature overnight. The reaction solution was concentrated and dried in a vacuum oven to give a crude product PA3008-1 (510 mg).

Step 2) Synthesis of Target Compound PA3008-2:

The compound PA300-1 (500 mg, 0.86 mmol) was dissolved in pyridine (5 mL), to which isopropyl chloroformate (0.1 mL, 0.86 mmol) was slowly added dropwise under an ice bath. When the dropwise addition was completed, the reaction solution was stirred at room temperature for 4 h. Then, the remaining half of isopropyl choroformate (0.1 mL, 0.86 mmol) was slowly added dropwise to the reaction solution. When the dropwise addition was completed, the reaction solution was stirred at room temperature overnight. The reaction solution was concentrated and a saturated aqueous sodium chloride solution (10 mL) was added. The reaction solution was extracted with ethyl acetate (3×30 mL), dried over anhydrous Na2SO4, filtered, and dried by rotary evaporation. The residue was separated and purified by silica gel chromatography column (eluent: DCM:MeOH (V:V)=50:1) to give a white solid PA3008-2 (520 mg) with a yield of 87%.

Step 3) Synthesis of Target Compound PA3008:

The compound PA3008-2 (200 mg, 3.02 mmol) was dissolved in 9% hydrochloric acid-ethanol solution (10 ml), and the mixture was stirred and reacted at room temperature for 16 hours. After the reaction was finished, the resulting product was neutralized with a saturated NaHCO$_3$ solution to a neutral pH value. The ethanol was removed by rotary evaporation, and then the residue was extracted with ethyl acetate (3×300 mL). The organic phase was washed with saturated brine, dried over anhydrous sodium sulfate, filtered, and dried by rotary evaporation. The residue was purified by Combiflash chromatography column to give a pale white solid PA3008 (120 mg) with a yield of 65%.

Example 9: PA3009

Synthetic Route:

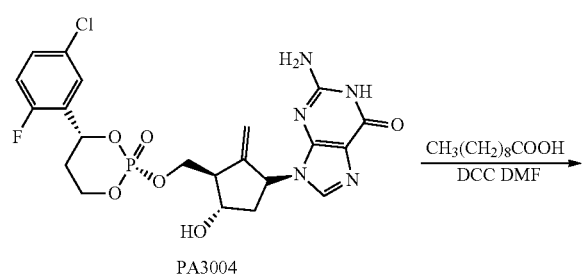

PA3004

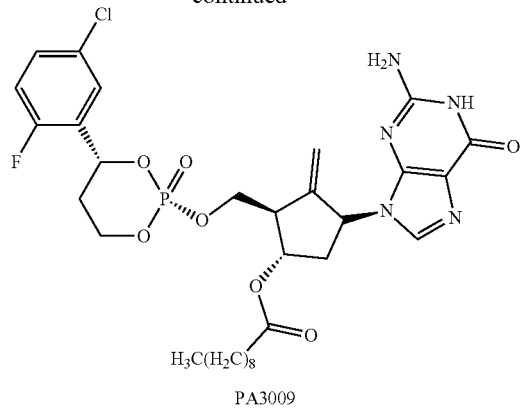

PA3009

Experimental Section:

Step 1) Synthesis of Compound PA3009:

The compound PA3004 (300 mg, 0.57 mmol) was dissolved in DMF (10 ml), to which DCC (352 mg, 1.71 mmol), decanoic acid (117 mg, 0.68 mmol), and a catalytic amount of DMAP (10 mg) were added at room temperature. Then, the reaction solution was stirred at room temperature overnight. The reaction was quenched with a saturated aqueous sodium chloride solution (40 mL). The resulting product was extracted with ethyl acetate (3×50 mL), dried over anhydrous Na2SO4, filtered, and dried by rotary evaporation. The residue was purified by Combiflash chromatography column to give a white solid PA3009 (243 mg) with a yield of 63%.

Example 10: PA3010

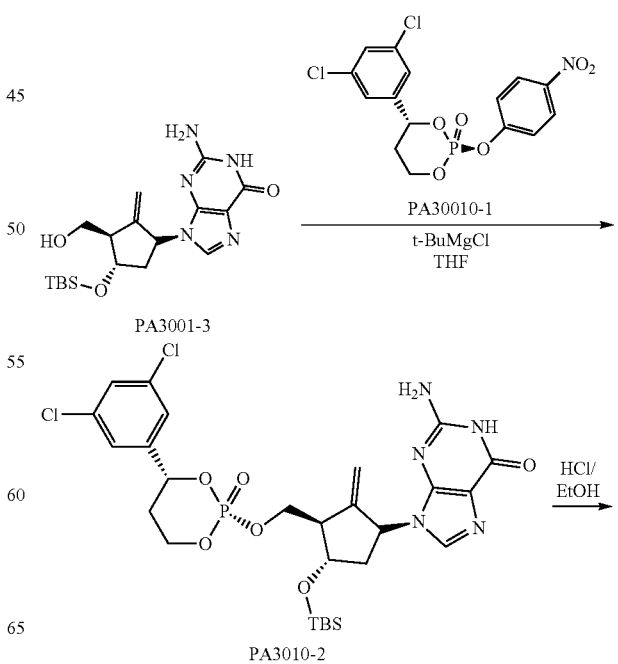

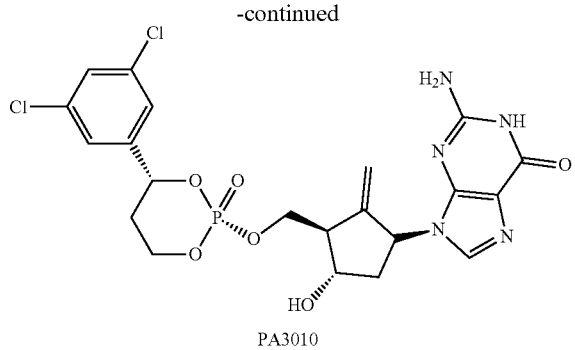

PA3010

Synthetic Route:
Experimental Section:
Step 1) Synthesis of Compound PA3010-2:

The compound PA3001-3 (300 mg, 0.77 mmol) was dissolved in tetrahydrofuran (5 ml), to which a 1M tert-butylmagnesium chloride solution (2.7 mL, 2.7 mmol, 3.5 eq) was slowly added dropwise under an ice bath. When the dropwise addition was completed, the reaction solution was stirred at room temperature for 2 hour and then cooled to 0° C. PA3010-1 (370 mg, 0.92 mmol) was added. Then, the reaction solution was stirred at room temperature overnight. The reaction was quenched with a saturated aqueous ammonium chloride solution (30 mL). The resulting product was extracted with ethyl acetate (3×100 mL), dried over anhydrous Na2SO4, filtered, and dried by rotary evaporation. The residue was separated and purified by silica gel chromatography column (eluent: DCM:MeOH (V:V)=20:1) to give a white solid PA3010-2 (300 mg) with a yield of 66%.

Step 2) Synthesis of Target Compound PA3010:

The compound PA3010-2 (300 mg, 0.47 mmol) was dissolved in 3.6% hydrochloric acid-ethanol solution (10 ml), and the mixture was stirred and reacted at room temperature for 2 hours. After the reaction was finished, the resulting product was neutralized with a saturated NaHCO3 solution to a pH value of about 7.5. The ethanol was removed by rotary evaporation, and then the residue was extracted with ethyl acetate (3×80 mL). The organic phase was washed with saturated brine, dried over anhydrous sodium sulfate, filtered, and dried by rotary evaporation. The residue was separated and purified by silica gel chromatography column (eluent: DCM:MeOH (V:V)=20:1) to give a crude product. The crude product was purified by Combiflash chromatography column to give a white solid PA3010 (45 mg) with a yield of 18%.

Example 11: PA3011

Synthetic Route:

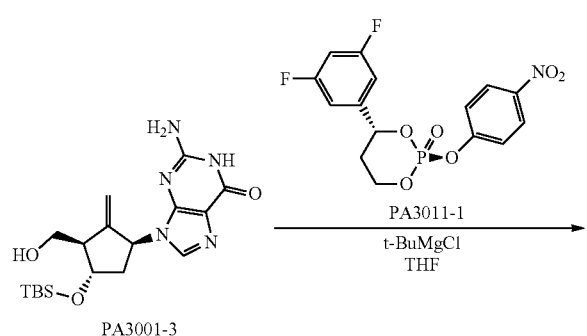

PA3001-3

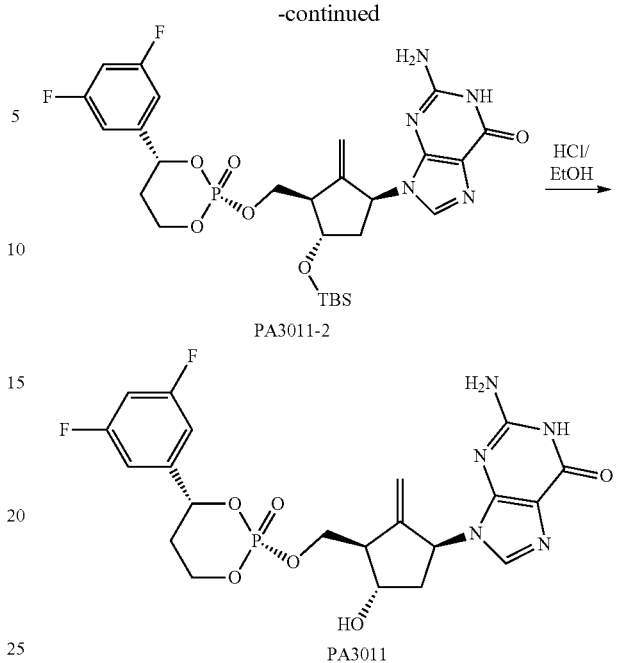

PA3011-2

PA3011

Experimental Section:
Step 1) Synthesis of Compound PA3011-2

The compound PA3001-3 (300 mg, 0.77 mmol) was dissolved in tetrahydrofuran (5 ml), to which a 1M tert-butylmagnesium chloride solution (2.7 mL, 2.7 mmol, 3.5 eq) was slowly added dropwise under an ice bath. When the dropwise addition was completed, the reaction solution was stirred at room temperature for 2 hours and then cooled to 0° C. PA3011-1 (0.37 g, 0.99 mmol, 1.3 eq) was added. Then, the reaction solution was stirred at room temperature overnight. The reaction was quenched with a saturated aqueous ammonium chloride solution (30 mL). The resulting product was extracted with ethyl acetate (3×100 mL), dried over anhydrous Na2SO4, filtered, and dried by rotary evaporation. The residue was separated and purified by silica gel chromatography column (eluent: DCM:MeOH (V:V)=20/1) to give a white solid PA3011-2 (320 mg) with a yield of 65%.

Step 2) Synthesis of Target Compound PA3011

The compound PA3011-2 (0.32 g, 0.5 mmol) was dissolved in 3.6% hydrochloric acid-ethanol solution (10 ml), and the mixture was stirred and reacted at room temperature for 2 hours. After the reaction was finished, the resulting product was neutralized with a saturated NaHCO3 solution to a pH value of about 7.5. The ethanol was removed by rotary evaporation, and then the residue was extracted with ethyl acetate (3×80 mL). The organic phase was washed with saturated brine, dried over anhydrous sodium sulfate, filtered, and dried by rotary evaporation. The residue was separated and purified by silica gel chromatography column (eluent: DCM:MeOH (V:V)=20:1) to give a crude product. The crude product was purified by Combiflash chromatography column to give a white solid PA3011 (115 mg) with a yield of 44%.

Example 12: PA3012

Synthetic Route:

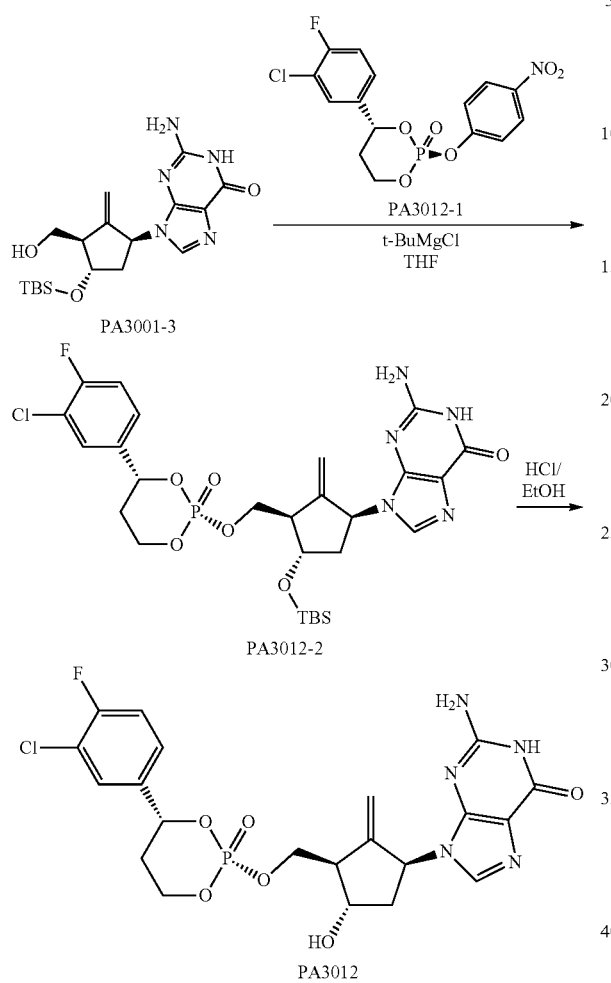

Experimental Section:

Step 1) Synthesis of Compound PA3012-2:

The compound PA3001-3 (300 mg, 0.77 mmol) was dissolved in tetrahydrofuran (5 ml), to which a 1M tert-butylmagnesium chloride solution (2.7 mL, 2.7 mmol, 3.5 eq) was slowly added dropwise under an ice bath. When the dropwise addition was completed, the reaction solution was stirred at room temperature for 2 hours and then cooled to 0° C. PA3012-1 (446 mg, 1.2 mmol) was added. Then, the reaction solution was stirred at room temperature overnight. The reaction was quenched with a saturated aqueous ammonium chloride solution (30 mL). The resulting product was extracted with ethyl acetate (3×100 mL), dried over anhydrous Na2SO4, filtered, and dried by rotary evaporation. The residue was separated and purified by silica gel chromatography column (eluent: DCM:MeOH (V:V)=20:1) to give a white solid PA3012-2 (300 mg) with a yield of 66%.

Step 2) Synthesis of Target Compound PA3012:

The compound PA3012-2 (300 mg, 0.47 mmol) was dissolved in 3.6% hydrochloric acid-ethanol solution (10 ml), and the mixture was stirred and reacted at room temperature for 2 hours. After the reaction was finished, the resulting product was neutralized with a saturated NaHCO₃ solution to a pH value of about 7.5. The ethanol was removed by rotary evaporation, and then the residue was extracted with ethyl acetate (3×60 mL). The organic phase was washed with saturated brine, dried over anhydrous sodium sulfate, filtered, and dried by rotary evaporation. The residue was separated and purified by silica gel chromatography column (eluent: DCM:MeOH (V:V)=20:1) to give a crude product. The crude product was purified by Combi-flash chromatography column to give a pale white solid PA3012 (45 mg) with a yield of 18%.

Example 13: PA3013

Synthetic Route:

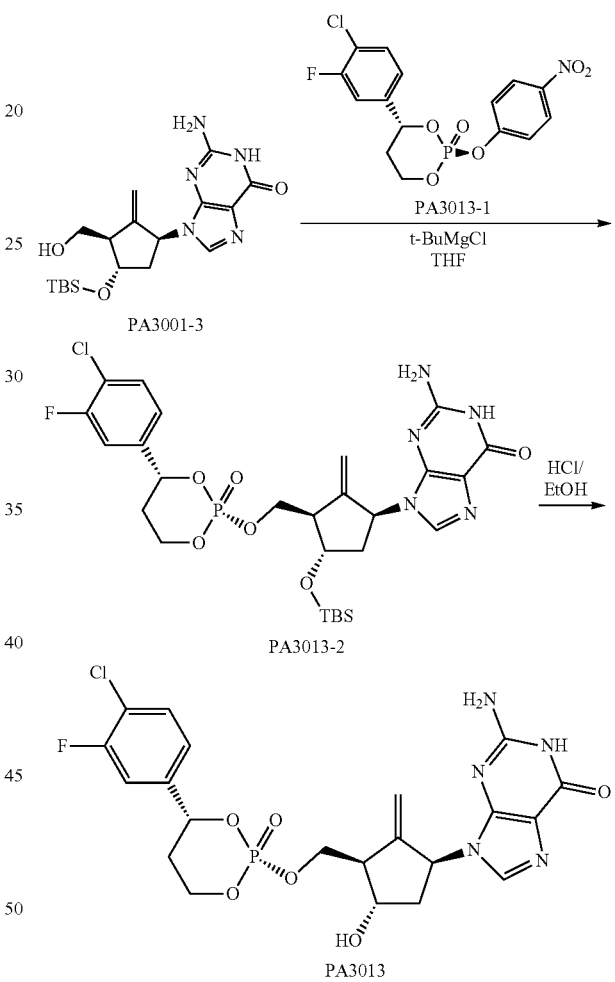

Experimental Section:

Step 1) Synthesis of Compound PA3013-2:

The compound PA3001-3 (300 mg, 0.77 mmol) was dissolved in tetrahydrofuran (10 ml), to which a 1M tert-butylmagnesium chloride solution (2.7 mL, 2.7 mmol, 3.5 eq) was slowly added dropwise under an ice bath. When the dropwise addition was completed, the reaction solution was stirred at room temperature for 2 hours and then cooled to 0° C. PA3013-1 (446 mg, 1.2 mmol) was added. Then, the reaction solution was stirred at room temperature overnight. The reaction was quenched with a saturated aqueous ammonium chloride solution (30 mL). The resulting product was extracted with ethyl acetate (3×100 mL), dried over anhydrous Na2SO4, filtered, and dried by rotary evaporation. The residue was separated and purified by silica gel chromatography column (eluent: DCM:MeOH (V:V)=20:1) to give a white solid PA3013-2 (350 mg) with a yield of 71%.

Step 2) Synthesis of Target Compound PA3013:

The compound PA3013-2 (350 mg, 0.55 mmol) was dissolved in 3.6% hydrochloric acid-ethanol solution (15 ml), and the mixture was stirred and reacted at room temperature for 2 hours. After the reaction was finished, the resulting product was neutralized with a saturated NaHCO$_3$ solution to a neutral pH value. The ethanol was removed by rotary evaporation, and then the residue was extracted with ethyl acetate (2×60 mL). The organic phase was washed with saturated brine, dried over anhydrous sodium sulfate, filtered, and dried by rotary evaporation. The residue was separated and purified by silica gel chromatography column (eluent: DCM:MeOH (V:V)=20:1), purified by preparative plate (developing agent: DCM:MeOH (V:V)=10:1), and purified by Combiflash chromatography column to give a pale white solid PA3013 (20 mg) with a yield of 7%.

Example 14: PA3014

Synthetic Route:

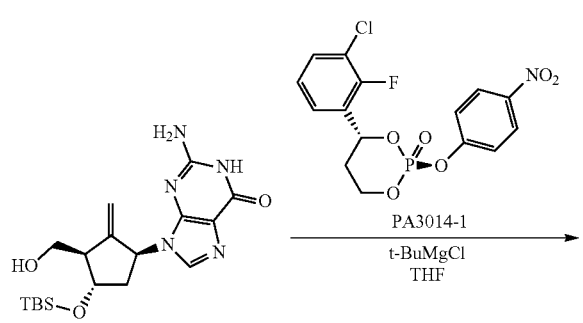

Experimental Section:

Step 1) Synthesis of Compound PA3014-2:

The compound PA3001-3 (230 mg, 0.58 mmol) was dissolved in tetrahydrofuran (20 ml), to which a 1M tert-butylmagnesium chloride solution (1.75 mL, 1.75 mmol, 5.5 eq) was slowly added dropwise under an ice bath. When the dropwise addition was completed, the reaction solution was stirred at room temperature for 1 hour and then cooled to 0° C. PA3014-1 (0.27 g, 0.69 mmol, 1.3 eq) was added. Then, the reaction solution was stirred at room temperature overnight. The reaction was quenched with a saturated aqueous ammonium chloride solution (20 mL). The resulting product was extracted with ethyl acetate (3×100 mL), dried over anhydrous Na2SO4, filtered, and dried by rotary evaporation. The residue was separated and purified by silica gel chromatography column (eluent: DCM:MeOH (V:V)=20:1) to give a white solid PA3014-2 (298 mg) with a yield of 79%.

Step 2) Synthesis of Target Compound PA3014:

The compound PA3014-2 (298 mg, 0.46 mmol) was dissolved in 3.6% hydrochloric acid-ethanol solution (3.5 ml), and the mixture was stirred and reacted at room temperature for 2 hours. After the reaction was finished, the resulting product was neutralized with a saturated NaHCO$_3$ solution to a neutral pH value. The ethanol was removed by rotary evaporation, and then the residue was extracted with ethyl acetate (2×60 mL). The organic phase was washed with saturated brine, dried over anhydrous sodium sulfate, filtered, and dried by rotary evaporation. The residue was purified by Combiflash chromatography column to give a pale white solid PA3014 (61 mg) with a yield of 36%.

Example 15: PA3016

Synthetic Route:

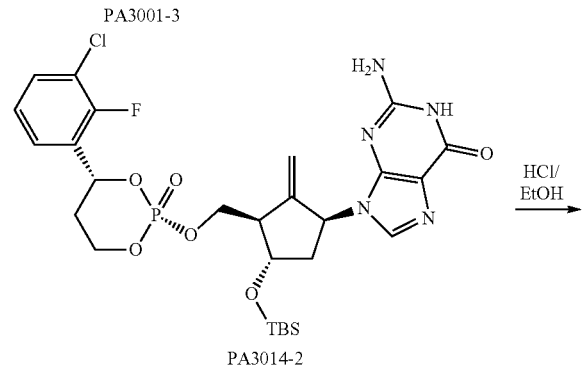

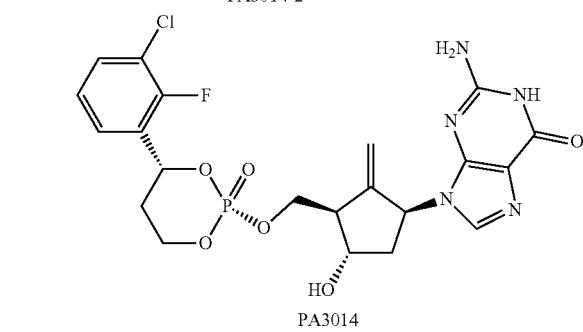

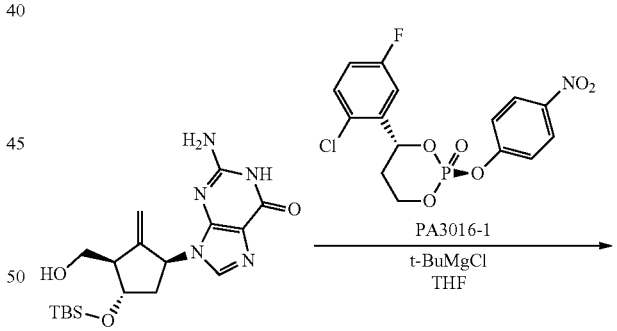

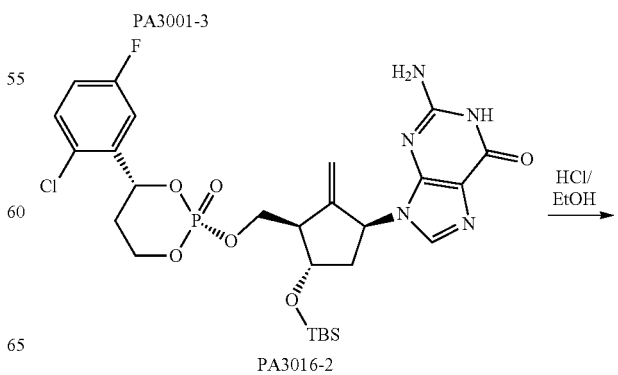

-continued

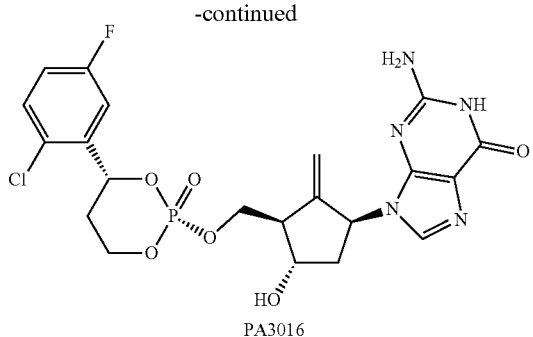

PA3016

Experimental Section:

Step 1) Synthesis of Compound PA3016-2:

The compound PA3001-3 (230 mg, 0.59 mmol) was dissolved in tetrahydrofuran (10 ml), to which a 1M tert-butylmagnesium chloride solution (2.1 mL, 2.1 mmol, 3.5 eq) was slowly added dropwise under an ice bath. When the dropwise addition was completed, the reaction solution was stirred at room temperature for 2 hours and then cooled to 0° C. PA3016-1 (340 mg, 0.88 mmol) was added. Then, the reaction solution was stirred at room temperature overnight. The reaction was quenched with a saturated aqueous ammonium chloride solution (30 mL). The resulting product was extracted with ethyl acetate (3×100 mL), dried over anhydrous Na2SO4, filtered, and dried by rotary evaporation. The residue was separated and purified by silica gel chromatography column (eluent: DCM:MeOH (V:V)=20:1) to give a white solid PA3016-2 (250 mg) with a yield of 66%.

Step 2) Synthesis of Target Compound PA3016:

The compound PA3016-2 (250 mg, 0.39 mmol) was dissolved in 3.6% hydrochloric acid-ethanol solution (15 ml), and the mixture was stirred and reacted at room temperature for 2 hours. After the reaction was finished, the resulting product was neutralized with a saturated NaHCO3 solution to a neutral pH value. The ethanol was removed by rotary evaporation, and then the residue was extracted with ethyl acetate (2×60 mL). The organic phase was washed with saturated brine, dried over anhydrous sodium sulfate, filtered, and dried by rotary evaporation. The residue was separated and purified by silica gel chromatography column (eluent: DCM:MeOH (V:V)=20:1) and purified by Combi-flash chromatography column to give a pale white solid PA3016 (20 mg) with a yield of 51%.

Example 16: PA3017

Synthetic Route:

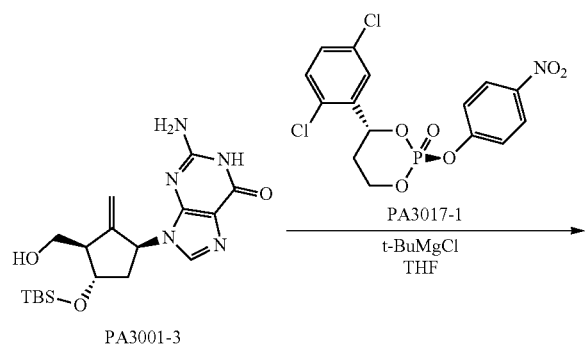

-continued

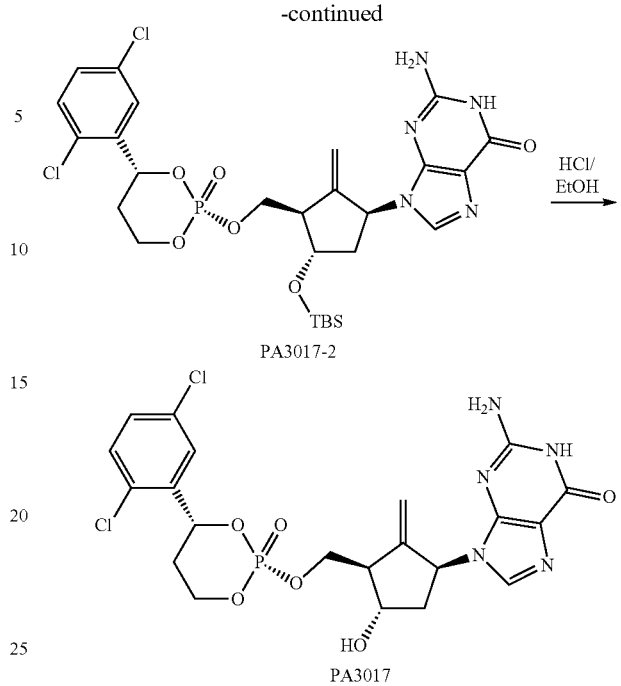

Experimental Section:

Step 1) Synthesis of Compound PA3017-2:

The compound PA3001-3 (300 mg, 0.77 mmol) was dissolved in tetrahydrofuran (5 ml), to which a 1M tert-butylmagnesium chloride solution (2.7 mL, 2.7 mmol, 3.5 eq) was slowly added dropwise under an ice bath. When the dropwise addition was completed, the reaction solution was stirred at room temperature for 2 hours and then cooled to 0° C. PA3017-1 (446 mg, 1.2 mmol) was added. Then, the reaction solution was stirred at room temperature overnight. The reaction was quenched with a saturated aqueous ammonium chloride solution (30 mL). The resulting product was extracted with ethyl acetate (3×100 mL), dried over anhydrous Na2SO4, filtered, and dried by rotary evaporation. The residue was separated and purified by silica gel chromatography column (eluent: DCM:MeOH (V:V)=20:1) to give a white solid PA3017-2 (300 mg) with a yield of 66%.

Step 2) Synthesis of Target Compound PA3017:

The compound PA3017-2 (300 mg, 0.47 mmol) was dissolved in 3.6% hydrochloric acid-ethanol solution (10 ml), and the mixture was stirred and reacted at room temperature for 2 hours. After the reaction was finished, the resulting product was neutralized with a saturated NaHCO3 solution to a pH value of about 7.5. The ethanol was removed by rotary evaporation, and then the residue was extracted with ethyl acetate (3×60 mL). The organic phase was washed with saturated brine, dried over anhydrous sodium sulfate, filtered, and dried by rotary evaporation. The residue was separated and purified by silica gel chromatography column (eluent: DCM:MeOH (V:V)=20:1) to give a crude product. The crude product was purified by Combi-flash chromatography column to give a pale white solid PA3017 (80 mg) with a yield of 28%.

Example 17: PA3018

Synthetic Route:

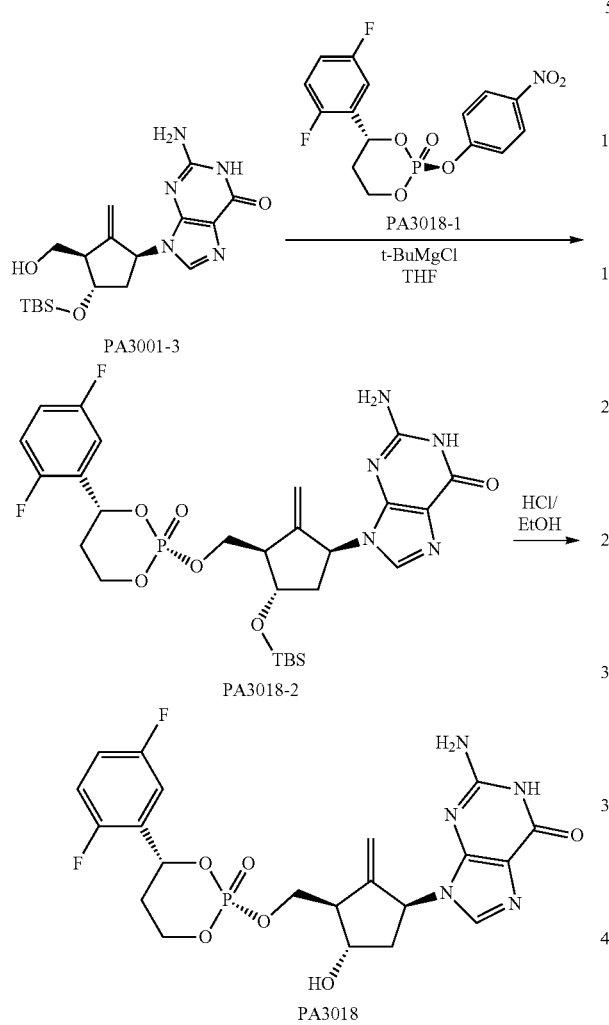

Experimental Section:

Step 1) Synthesis of Compound PA3018-2:

The compound PA3001-3 (391 mg, 1.0 mmol) was dissolved in tetrahydrofuran (40 ml), to which a 1M tert-butylmagnesium chloride solution (3.5 mL, 3.5 mmol) was slowly added dropwise under an ice bath. When the dropwise addition was completed, the reaction solution was stirred at room temperature for 1 hour and then cooled to 0° C. PA3018-1 (371 mg, 1.0 mmol) was added. Then, the reaction solution was stirred at room temperature overnight. The reaction was quenched with a saturated aqueous ammonium chloride solution (30 mL). The resulting product was extracted with ethyl acetate (3×70 mL), dried over anhydrous Na2SO4, filtered, and dried by rotary evaporation. The residue was separated and purified by silica gel chromatography column (eluent: DCM:MeOH (V:V)=20:1) to give a white solid PA3018-2 (262 mg) with a yield of 42%.

Step 2) Synthesis of Target Compound PA3018:

The compound PA3018-2 (262 mg, 0.42 mmol) was dissolved in 3.6% hydrochloric acid-ethanol solution (10 ml), and the mixture was stirred and reacted at room temperature for 2 hours. After the reaction was finished, the resulting product was neutralized with a saturated NaHCO3 solution to a neutral pH value. The ethanol was removed by rotary evaporation, and then the residue was extracted with ethyl acetate (3×60 mL). The organic phase was washed with saturated brine, dried over anhydrous sodium sulfate, filtered, and dried by rotary evaporation. The residue was purified by Combiflash chromatography column to give a white solid PA3018 (96 mg) with a yield of 45%.

Example 18: PA3019

Synthetic Route:

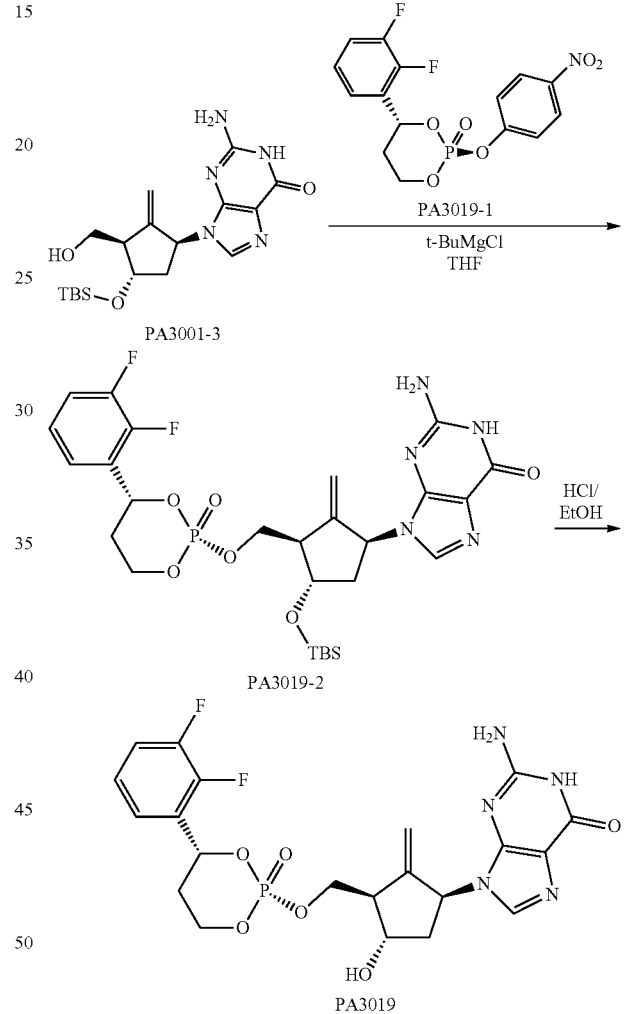

Experimental Section:

Step 1) Synthesis of Compound PA3019-2:

The compound PA3001-3 (200 mg, 0.51 mmol) was dissolved in tetrahydrofuran (10 ml), to which a 1M tert-butylmagnesium chloride solution (1.8 mL, 1.8 mmol) was slowly added dropwise under an ice bath. When the dropwise addition was completed, the reaction solution was stirred at room temperature for 1 hour and then cooled to 0° C. PA3019-1 (285 mg, 0.77 mmol) was added. Ten, the reaction solution was stirred at room temperature overnight. The reaction was quenched with a saturated aqueous ammonium chloride solution (30 mL). The resulting product was extracted with ethyl acetate (3×150 mL), dried over anhydrous Na2SO4, filtered, and dried by rotary evaporation. The residue was separated and purified by silica gel chromatography column (eluent: DCM:MeOH (V:V)=10:1) to give a white solid PA3019-2 (180 mg) with a yield of 56%.

Step 2) Synthesis of Target Compound PA3019:

The compound PA3019-2 (180 mg, 0.29 mmol) was dissolved in 3.6% hydrochloric acid-ethanol solution (15 ml), and the mixture was stirred and reacted at room temperature for 2 hours. After the reaction was finished, the resulting product was neutralized with a saturated NaHCO$_3$ solution to a neutral pH value. The ethanol was removed by rotary evaporation, and then the residue was extracted with ethyl acetate (3×100 mL). The organic phase was washed with saturated brine, dried over anhydrous sodium sulfate, filtered, and dried by rotary evaporation. The residue was purified by Combiflash chromatography column to give a pale white solid PA3019 (20 mg) with a yield of 13.5%.

Example 19: PA3020

Synthetic Route:

Experimental Section:
Step 1) Synthesis of Compound PA3020-2:

The compound PA3001-3 (200 mg, 0.52 mmol) was dissolved in tetrahydrofuran (5 ml), to which a 1M tert-butylmagnesium chloride solution (1.8 mL, 1.8 mmol, 3.5 eq) was slowly added dropwise under an ice bath. When the dropwise addition was completed, the reaction solution was stirred at room temperature for 2 hours and then cooled to 0° C. PA3020-1 (190 mg, 0.52 mmol) was added. Then, the reaction solution was stirred at room temperature overnight. The reaction was quenched with a saturated aqueous ammonium chloride solution (20 mL). The resulting product was extracted with ethyl acetate (3×80 mL), dried over anhydrous Na2SO4, filtered, and dried by rotary evaporation. The residue was separated and purified by silica gel chromatography column (eluent: DCM:MeOH (V:V)=20:1) to give a white solid PA3020-2 (170 mg) with a yield of 53%.

Step 2) Synthesis of Target Compound PA3020:

The compound PA3020-2 (170 mg, 0.27 mmol) was dissolved in 3.6% hydrochloric acid-ethanol solution (10 ml), and the mixture was stirred and reacted at room temperature for 2 hours. After the reaction was finished, the resulting product was neutralized with a saturated NaHCO$_3$ solution to a pH value of about 7.5. The ethanol was removed by rotary evaporation, and then the residue was extracted with ethyl acetate (3×60 mL). The organic phase was washed with saturated brine, dried over anhydrous sodium sulfate, filtered, and dried by rotary evaporation. The residue was separated and purified by silica gel chromatography column (eluent: DCM:MeOH (V:V)=20:1) to give a crude product. The crude product was purified by Combiflash chromatography column to give a pale white solid PA3020 (25 mg) with a yield of 18%.

Example 20: PA3022

Synthetic Route:

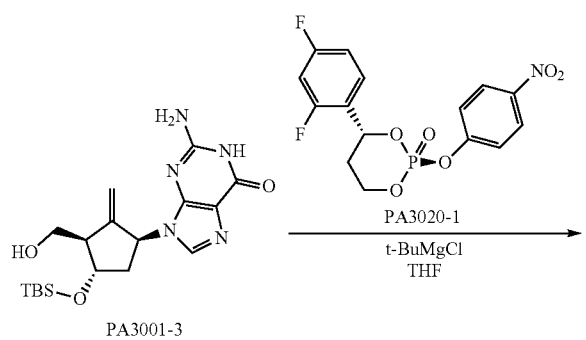

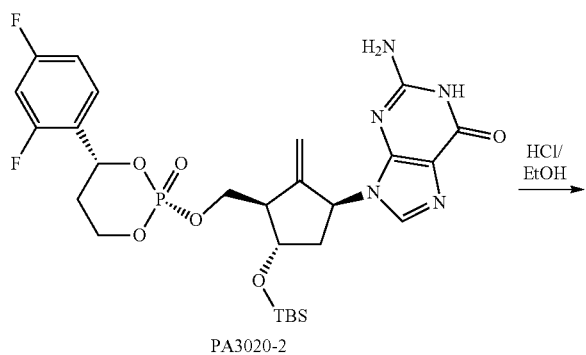

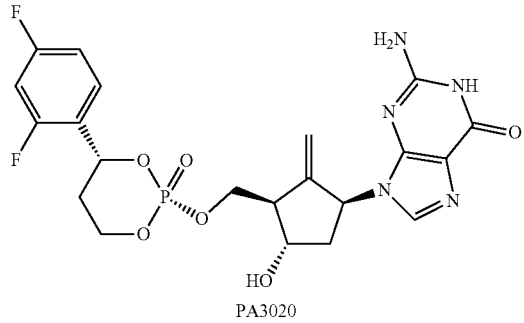

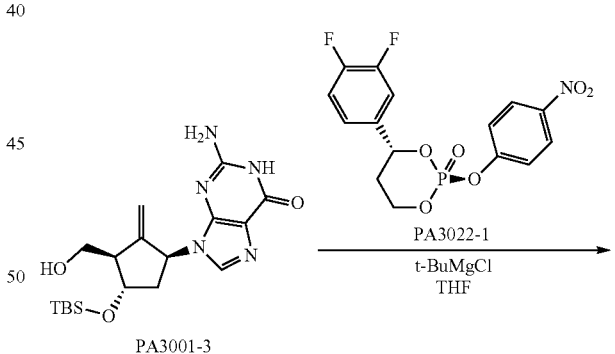

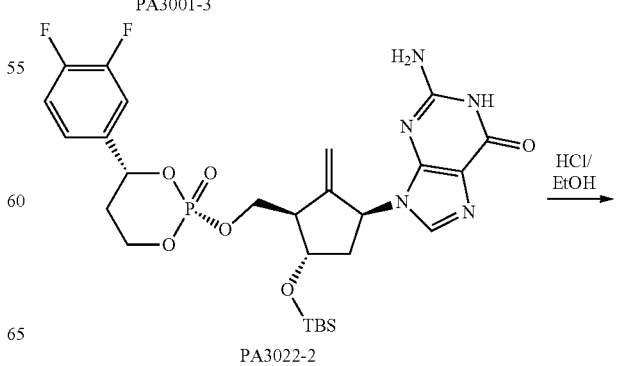

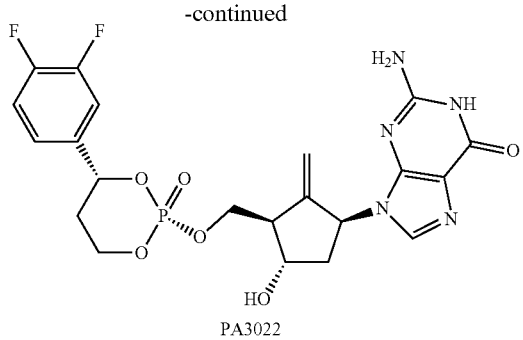

PA3022

Experimental Section:

Step 1) Synthesis of Compound PA3022-2:

The compound PA3001-3 (391 mg, 1.0 mmol) was dissolved in tetrahydrofuran (40 ml), to which a 1M tert-butylmagnesium chloride solution (3.5 mL, 3.5 mmol) was slowly added dropwise under an ice bath. When the dropwise addition was completed, the reaction solution was stirred at room temperature for 1 hour and then cooled to 0° C. PA3022-1 (371 mg, 1.0 mmol) was added. Then, the reaction solution was stirred at room temperature overnight. The reaction was quenched with a saturated aqueous ammonium chloride solution (30 mL). The resulting product was extracted with ethyl acetate (3×100 mL), dried over anhydrous Na2SO4, filtered, and dried by rotary evaporation. The residue was separated and purified by silica gel chromatography column (eluent: DCM:MeOH (V:V)=20:1) to give a white solid PA3022-2 (240 mg) with a yield of 38.5%.

Step 2) Synthesis of Target Compound PA3022:

The compound PA3022-2 (240 mg, 0.38 mmol) was dissolved in 3.6% hydrochloric acid-ethanol solution (10 ml), and the mixture was stirred and reacted at room temperature for 2 hours. After the reaction was finished, the resulting product was neutralized with a saturated NaHCO3 solution to a neutral pH value. The ethanol was removed by rotary evaporation, and then the residue was extracted with ethyl acetate (3×80 mL). The organic phase was washed with saturated brine, dried over anhydrous sodium sulfate, filtered, and dried by rotary evaporation. The residue was purified by Combiflash chromatography column to give a white solid PA3022 (103 mg) with a yield of 53%.

Example 21: PA3023

Synthetic Route:

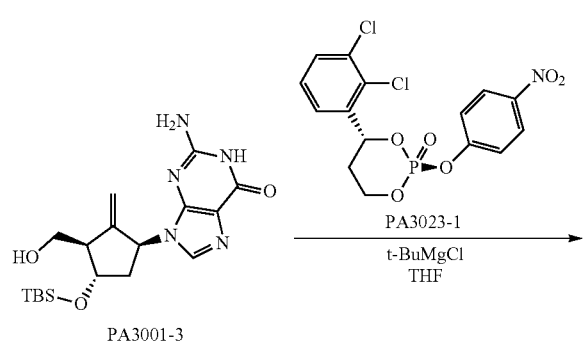

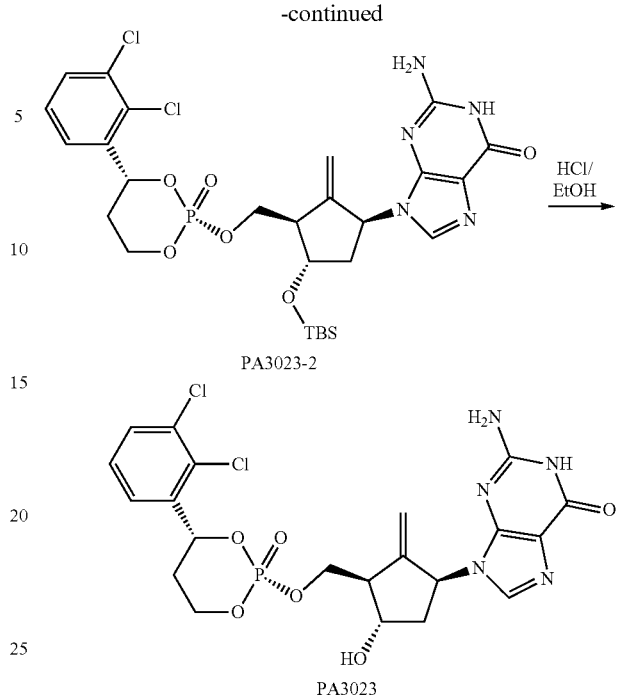

PA3023-2

PA3023

Experimental Section:

Step 1) Synthesis of Compound PA3023-2:

The compound PA3001-3 (200 mg, 0.51 mmol) was dissolved in tetrahydrofuran (10 ml), to which a 1M tert-butylmagnesium chloride solution (1.8 mL, 1.8 mmol) was slowly added dropwise under an ice bath. When the dropwise addition was completed, the reaction solution was stirred at room temperature for 1 hour and then cooled to 0° C. PA3023-1 (309 mg, 0.77 mmol) was added. Then, the reaction solution was stirred at room temperature overnight. The reaction was quenched with a saturated aqueous ammonium chloride solution (30 mL). The resulting product was extracted with ethyl acetate (3×150 mL), dried over anhydrous Na2SO4, filtered, and dried by rotary evaporation. The residue was separated and purified by silica gel chromatography column (eluent: DCM:MeOH (V:V)=10:1) to give a white solid PA3023-2 (120 mg) with a yield of 36%.

Step 2) Synthesis of Target Compound PA3023:

The compound PA3023-2 (120 mg, 0.18 mmol) was dissolved in 3.6% hydrochloric acid-ethanol solution (15 ml), and the mixture was stirred and reacted at room temperature for 2 hours. After the reaction was finished, the resulting product was neutralized with a saturated NaHCO3 solution to a neutral pH value. The ethanol was removed by rotary evaporation, and then the residue was extracted with ethyl acetate (3×100 mL). The organic phase was washed with saturated brine, dried over anhydrous sodium sulfate, filtered, and dried by rotary evaporation. The residue was purified by Combiflash chromatography column to give a pale white solid PA3023 (22 mg) with a yield of 22%.

Example 22: PA3024

Synthetic Route:

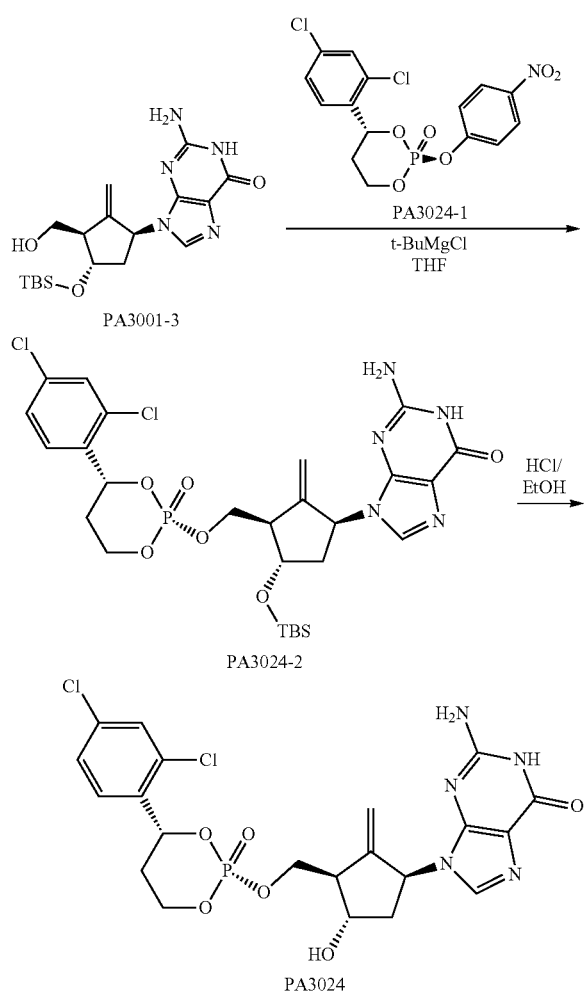

Experimental Section:
Step 1) Synthesis of Compound PA3024-2:

The compound PA3001-3 (200 mg, 0.52 mmol) was dissolved in tetrahydrofuran (5 ml), to which a 1M tert-butylmagnesium chloride solution (1.8 mL, 1.8 mmol, 3.5 eq) was slowly added dropwise under an ice bath. When the dropwise addition was completed, the reaction solution was stirred at room temperature for 2 hours and then cooled to 0° C. PA3024-1 (200 mg, 0.52 mmol) was added. Then, the reaction solution was stirred at room temperature overnight. The reaction was quenched with a saturated aqueous ammonium chloride solution (20 mL). The resulting product was extracted with ethyl acetate (3×80 mL), dried over anhydrous Na2SO4, filtered, and dried by rotary evaporation. The residue was separated and purified by silica gel chromatography column (eluent: DCM:MeOH (V:V)=20:1) to give a white solid PA3024-2 (150 mg) with a yield of 45%.

Step 2) Synthesis of Target Compound PA3024:

The compound PA3024-2 (150 mg, 0.23 mmol) was dissolved in 3.6% hydrochloric acid-ethanol solution (10 ml), and the mixture was stirred and reacted at room temperature for 2 hours. After the reaction was finished, the resulting product was neutralized with a saturated NaHC3 solution to a pH value of about 7.5. The ethanol was removed by rotary evaporation, and then the residue was extracted with ethyl acetate (3×60 mL). The organic phase was washed with saturated brine, dried over anhydrous sodium sulfate, filtered, and dried by rotary evaporation. The residue was separated and purified by silica gel chromatography column (eluent: DCM:MeOH (V:V)=20:1) to give a crude product. The crude product was purified by Combi-flash chromatography column to give a pale white solid PA3024 (80 mg) with a yield of 65%.

Example 23: PA3026

Synthetic Route:

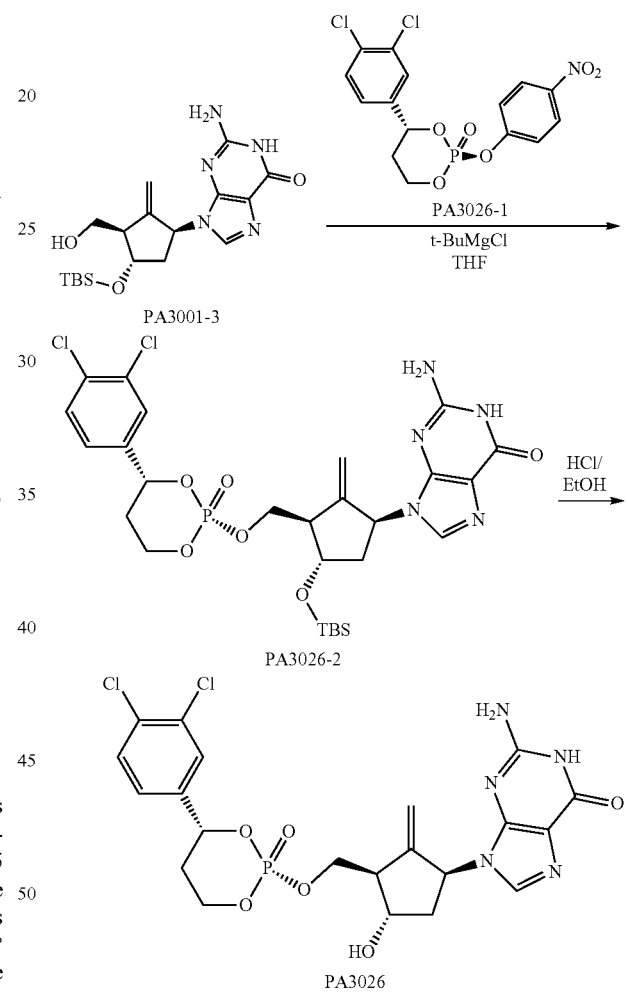

Experimental Section:
Step 1) Synthesis of Compound PA3026-2:

The compound PA3001-3 (391 mg, 1.0 mmol) was dissolved in tetrahydrofuran (40 ml), to which a 1M tert-butylmagnesium chloride solution (3.5 mL, 3.5 mmol) was slowly added dropwise under an ice bath. When the dropwise addition was completed, the reaction solution was stirred at room temperature for 1 hour and then cooled to 0° C. PA3026-1 (402 ng, 1.0 mmol) was added. Then, the reaction solution was stirred at room temperature overnight. The reaction was quenched with a saturated aqueous ammonium chloride solution (30 mL). The resulting product was extracted with ethyl acetate (3×100 mL), dried over anhydrous Na2SO4, filtered, and dried by rotary evaporation. The residue was separated and purified by silica gel chromatography column (eluent: DCM:MeOH (V:V)=20:1) to give a white solid PA3026-2 (100 mg) with a yield of 15.3%.

Step 2) Synthesis of Target Compound PA3026:

The compound PA3026-2 (100 mg, 0.15 mmol) was dissolved in 3.6% hydrochloric acid-ethanol solution (10 ml), and the mixture was stirred and reacted at room temperature for 2 hours. After the reaction was finished, the resulting product was neutralized with a saturated NaHCO3 solution to a neutral pH value. The ethanol was removed by rotary evaporation, and then the residue was extracted with ethyl acetate (3×60 mL). The organic phase was washed with saturated brine, dried over anhydrous sodium sulfate, filtered, and dried by rotary evaporation. The residue was purified by Combiflash chromatography column to give white solid PA3026 (32 mg) with a yield of 32.5%.

TABLE 1

The compounds prepared in the examples were shown in the following table

| Compound Number | Structural Formula | Molecular Weight |
|---|---|---|
| PA3001 | | 507.86 |
| PA3002 | | 525.85 |
| PA3003 | | 474.41 |
| PA3004 | | 525.85 |

TABLE 1-continued
The compounds prepared in the examples were shown in the following table
| Compound Number | Structural Formula | Molecular Weight |
|---|---|---|
| PA3005 | 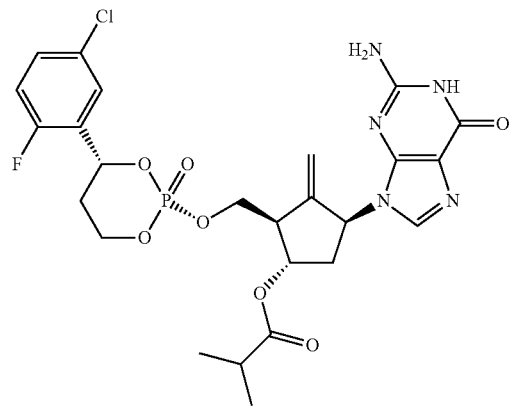 | 595.94 |
| PA3006 | 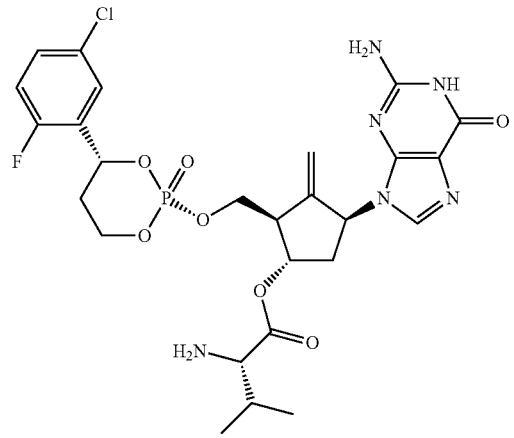 | 624.99 |
| PA3007 | 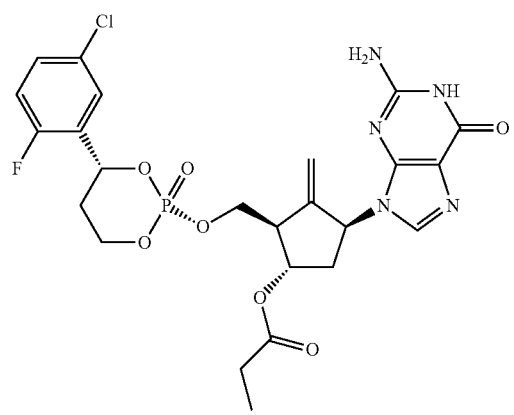 | 581.92 |

TABLE 1-continued

The compounds prepared in the examples were shown in the following table

| Compound Number | Structural Formula | Molecular Weight |
|---|---|---|
| PA3008 | | 611.94 |
| PA3009 | | 680.10 |
| PA3010 | | 542.31 |
| PA3011 | | 509.41 |

TABLE 1-continued

The compounds prepared in the examples were shown in the following table

| Compound Number | Structural Formula | Molecular Weight |
|---|---|---|
| PA3012 | | 525.86 |
| PA3013 | | 525.86 |
| PA3014 | | 525.86 |
| PA3016 | | 525.86 |

TABLE 1-continued

The compounds prepared in the examples were shown in the following table

| Compound Number | Structural Formula | Molecular Weight |
|---|---|---|
| PA3017 | | 542.31 |
| PA3018 | | 509.41 |
| PA3019 | | 509.41 |
| PA3020 | | 509.41 |

TABLE 1-continued

The compounds prepared in the examples were shown in the following table

| Compound Number | Structural Formula | Molecular Weight |
|---|---|---|
| PA3022 | | 509.41 |
| PA3023 | | 542.31 |
| PA3024 | | 542.31 |
| PA3026 | | 542.31 |

TABLE 2

NMR data on the compounds prepared in the examples were shown in the following table

| Number | NMR Data |
|---|---|
| PA3001 Comparative Example | $^1$H NMR (400 MHz, DMSO-$d_6$) δ: 10.56 (s, 1H), 7.69 (s, 1H), 7.51 (s, 1H), 7.49-7.40 (m, 3H), 6.42 (s, 2H), 5.73 (d, J = 10.6 Hz, 1H), 5.41-5.37 (m, 1H), 5.22 (s, 1H), 5.14 (d, J = 3.1 Hz, 1H), 4.65 (s, 1H), 4.61-4.41 (m, 2H), 4.35-4.18 (m, 3H), 2.79 (s, 1H), 2.38-2.16 (m, 3H), 2.14-2.03 (m, 1H)ppm. |

TABLE 2-continued

NMR data on the compounds prepared in the examples were shown in the following table

| Number | NMR Data |
|---|---|
| PA3002 | ¹H NMR (400 MHz, DMSO-$d_6$) δ: 10.57 (s, 1H), 7.68 (s, 1H), 7.49-7.43 (m, 1H), 7.40 (s, 1H), 7.35-7.27 (m, 1H), 6.42 (s, 2H), 5.79-5.71 (m, 1H), 5.44-5.35 (m, 1H), 5.22 (s, 1H), 5.14 (d, J = 3.3 Hz, 1H), 4.65 (s, 1H), 4.57-4.43 (m, 2H), 4.34-4.19 (m, 3H), 2.79 (s, 1H), 2.36-2.20 (m, 3H), 2.13-2.03 (m, 1H)ppm. |
| PA3003 | ¹H NMR (400 MHz, DMSO-$d_6$) δ: 10.60 (s, 1H), 8.62 (d, J = 6.1 Hz, 2H), 7.69 (s, 1H), 7.44 (d, J = 6.0 Hz, 2H), 6.43 (s, 2H), 5.77 (d, J = 11.1 Hz, 1H), 5.44-5.33 (m, 1H), 5.21 (s, 1H), 5.15 (s, 1H), 4.65 (s, 1H), 4.62-4.40 (m, 2H), 4.37-4.16 (m, 3H), 2.79 (s, 1H), 2.36-2.16 (m, 3H), 2.12-2.01 (m, 1H)ppm. |
| PA3004 | ¹H NMR (400 MHz, CDCl$_3$) δ: 10.61 (s, 1H), 7.73 (s, 1H), 7.60 (dd, J = 6.2, 2.7 Hz, 1H), 7.53 (ddd, J = 8.7, 4.4, 2.7 Hz, 1H), 7.41-7.30 (m, 1H), 6.45 (s, 2H), 5.87 (d, J = 11.3 Hz, 1H), 5.40 (t, J = 9.1 Hz, 1H), 5.23 (s, 1H), 5.14 (s, 1H), 4.66 (s, 1H), 4.64-4.41 (m, 2H), 4.35-4.16 (m, 3H), 2.78 (s, 1H), 2.47-2.26 (m, 2H), 2.20-2.04 (m, 2H)ppm. |
| PA3005 | ¹H NMR (400 MHz, DMSO-$d_6$) δ 10.66 (s, 1H), 7.74 (d, J = 16.4 Hz, 1H), 7.61 (dd, J = 6.2, 2.6 Hz, 1H), 7.57-7.48 (m, 1H), 7.41-7.30 (m, 1H), 6.45 (s, 2H), 5.89 (d, J = 11.6 Hz, 1H), 5.40-5.23 (m, 3H), 4.68 (d, J = 19.0 Hz, 1H), 4.61 (d, J = 7.0 Hz, 1H), 4.56-4.38 (m, 2H), 4.37-4.25 (m, 1H), 2.97 (s, 1H), 2.71-2.58 (m, 1H), 2.33-1.96 (m, 4H), 1.09 (t, J = 6.9 Hz, 6H)ppm |
| PA3006 | ¹H NMR (400 MHz, DMSO-$d_6$) δ 8.20 (s, 1H), 7.72 (s, 1H), 7.60 (dd, J = 6.2, 2.7 Hz, 1H), 7.57-7.49 (m, 1H), 7.41-7.30 (m, 1H), 6.44 (s, 2H), 5.88 (d, J = 11.2 Hz, 1H), 5.44-5.33 (m, 1H), 5.30 (s, 2H), 4.72 (s, 1H), 4.60 (d, J = 11.6 Hz, 1H), 4.54 -4.37 (m, 3H), 4.35-4.26 (m, 1H), 3.20 (d, J = 5.2 Hz, 1H), 2.99 (s, 1H), 2.67 (td, J = 13.9, 5.2 Hz, 1H), 2.27 (dd, J = 13.6, 7.8 Hz, 1H), 2.16 (d, J = 14.8 Hz, 1H), 1.85 (td, J = 13.5, 6.8 Hz, 1H), 0.86 (d, J = 3.3 Hz, 3H), 0.80 (d, J = 6.8 Hz, 3H)ppm |
| PA3007 | ¹H NMR (400 MHz, DMSO-$d_6$) δ 10.65 (s, 1H), 7.75 (s, 1H), 7.61 (dd, J = 6.2, 2.6 Hz, 1H), 7.57-7.48 (m, 1H), 7.41-7.30 (m, 1H), 6.48 (s, 2H), 5.89 (d, J = 11.4 Hz, 1H), 5.41-5.32 (m, 1H), 5.28 (s, 2H), 4.70 (s, 1H), 4.60 (d, J = 13.0 Hz, 1H), 4.54-4.24 (m, 3H), 2.98 (s, 1H), 2.70-2.55 (m, 1H), 2.43 (dd, J = 13.0, 8.7 Hz, 1H), 2.37-2.09 (m, 4H), 1.02 (t, J = 7.5 Hz, 3H)ppm |
| PA3008 | ¹H NMR (400 MHz, DMSO-$d_6$) δ 10.64 (s, 1H), 7.73 (s, 1H), 7.62 (dd, J = 6.1, 2.6 Hz, 1H), 7.54 (dd, J = 8.5, 4.1 Hz, 1H), 7.36 (t, J = 9.5 Hz, 1H), 6.47 (s, 2H), 5.89 (d, J = 11.2 Hz, 1H), 5.41-5.32 (m, 1H), 5.29 (s, 1H), 5.15 (d, J = 4.1 Hz, 1H), 4.77 (dt, J = 12.5, 6.3 Hz, 1H), 4.71-4.24 (m, 5H), 3.05 (s, 1H), 2.62 (td, J = 13.5, 4.6 Hz, 1H), 2.43 (dd, J = 18.8, 7.8 Hz, 1H), 2.31 (dd, J = 13.5, 7.4 Hz, 1H), 2.17 (d, J = 14.7 Hz, 1H), 1.22 (t, J = 6.4 Hz, 6H)ppm. |
| PA3009 | ¹H NMR (400 MHz, DMSO-$d_6$) δ 10.67 (s, 1H), 7.71 (s, 1H), 7.60 (dd, J = 6.2, 2.6 Hz, 1H), 7.56-7.48 (m, 1H), 7.40-7.29 (m, 1H), 6.46 (s, 2H), 5.89 (d, J = 11.2 Hz, 1H), 5.39-5.30 (m, 1H), 5.28 (s, 2H), 4.70 (s, 1H), 4.60 (d, J = 11.4 Hz, 1H), 4.54-4.25 (m, 3H), 2.98 (s, 1H), 2.69-2.55 (m, 1H), 2.47-2.36 (m, 1H), 2.34-2.11 (m, 4H), 1.50 (d, J = 6.4 Hz, 2H), 1.22 (s, 12H), 0.84 (t, J = 6.7 Hz, 3H)ppm. |
| PA3010 | ¹H NMR (400 MHz, DMSO) δ 10.59 (s, 1H), 7.69 (s, 1H), 7.63 (t, J = 1.9 Hz, 1H), 7.51 (t, J = 2.1 Hz, 2H), 6.43 (s, 2H), 5.79-5.70 (m, 1H), 5.40 (t, J = 9.0 Hz, 1H), 5.23 (s, 1H), 5.14 (d, J = 2.8 Hz, 1H), 4.66 (s, 1H), 4.59-4.41 (m, 2H), 4.34-4.16 (m, 3H), 2.79 (s, 1H), 2.38-2.17 (m, 3H), 2.09 (dd, J = 12.3, 8.1 Hz, 1H)ppm. |
| PA3011 | ¹H NMR (400 MHz, DMSO) δ 10.81-10.45 (m, 1H), 7.70 (d, J = 4.5 Hz, 1H), 7.27 (t, J = 9.3 Hz, 1H), 7.20 (d, J = 6.5 Hz, 2H), 6.47 (s, 2H), 5.75 (d, J = 9.7 Hz, 1H), 5.39 (t, J = 9.1 Hz, 1H), 5.22 (s, 1H), 5.17 (s, 1H), 4.64 (s, 1H), 4.51 (ddd, J = 33.7, 22.7, 10.8 Hz, 2H), 4.34-4.15 (m, 3H), 2.78 (s, 1H), 2.36-2.17 (m, 3H), 2.12-2.03 (m, 1H)ppm. |
| PA3012 | ¹H NMR (400 MHz, DMSO) δ 10.62 (s, 1H), 7.72 (s, 1H), 7.68 (d, J = 7.4 Hz, 1H), 7.48 (dd, J = 6.5, 1.4 Hz, 2H), 6.45 (s, 2H), 5.73 (d, J = 10.9 Hz, 1H), 5.39 (t, J = 9.2 Hz, 1H), 5.22 (s, 1H), 5.15 (s, 1H), 4.66 (s, 1H), 4.60-4.41 (m, 2H), 4.34-4.17 (m, 3H), 2.78 (s, 1H), 2.37-2.23 (m, 2H), 2.18 (d, J = 14.7 Hz, 1H), 2.13-2.03 (m, 1H)ppm |
| PA3013 | ¹H NMR (400 MHz, DMSO) δ 10.61 (s, 1H), 7.70 (d, J = 4.6 Hz, 1H), 7.69-7.63 (m, 1H), 7.52 (dd, J = 10.3, 2.2 Hz, 1H), 7.34 (d, J = 8.6 Hz, 1H), 6.45 (s, 2H), 5.75 (d, J = 10.6 Hz, 1H), 5.39 (t, J = 9.5 Hz, 1H), 5.22 (s, 1H), 5.16 (d, J = 3.0 Hz, 1H), 4.64 (s, 1H), 4.60-4.40 (m, 2H), 4.37-4.11 (m, 3H), 2.77 (s, 1H), 2.36-2.14 (m, 3H), 2.12-2.03 (m, 1H)ppm |
| PA3014 | ¹H NMR (400 MHz, DMSO) δ 10.58 (s, 1H), 7.68 (s, 1H), 7.67-7.62 (m, 1H), 7.55 (t, J = 6.5 Hz, 1H), 7.32 (t, J = 7.9 Hz, 1H), 6.42 (s, 2H), 5.92 (d, J = 11.2 Hz, 1H), 5.39 (t, J = 9.2 Hz, 1H), 5.21 (s, 1H), 5.13 (d, J = 2.9 Hz, 1H), 4.69-4.58 (m, 2H), 4.56-4.42 (m, 1H), 4.36-4.15 (m, 3H), 2.78 (s, 1H), 2.46-2.25 (m, 2H), 2.18 (d, J = 14.8 Hz, 1H), 2.12-2.01 (m, 1H)ppm |
| PA3016 | ¹H NMR (400 MHz, DMSO) δ 10.58 (s, 1H), 7.72-7.67 (m, 1H), 7.60 (dd, J = 8.9, 5.1 Hz, 1H), 7.49-7.40 (m, 1H), 7.33 (td, J = 8.5, 3.1 Hz, 1H), 6.43 (s, 2H), 5.86 (d, J = 11.1 Hz, 1H), 5.40 (t, J = 9.1 Hz, 1H), 5.25 (s, 1H), 5.16 (d, J = 3.1 Hz, 1H), 4.64 (d, J = 15.8 Hz, 2H), 4.56-4.43 (m, 1H), 4.40-4.21 (m, 3H), 2.80 (s, 1H), 2.39-2.24 (m, 2H), 2.20 (d, J = 14.5 Hz, 1H), 2.09 (dd, J = 12.9, 8.1 Hz, 1H)ppm. |
| PA3017 | ¹H NMR (400 MHz, DMSO) δ 10.86 (s, 1H), 8.04 (s, 1H), 7.63 (dd, J = 7.8, 2.6 Hz, 1H), 7.58 (d, J = 8.6 Hz, 1H), 7.52 (dd, J = 8.6, 2.5 Hz, 1H), 6.62 (s, 2H), 5.87 (d, J = 11.0 Hz, 1H), 5.43 (t, J = 8.9 Hz, 1H), 5.28 (s, 1H), 4.74 (s, 1H), 4.70-4.59 (m, 1H), 4.55-4.42 (m, 1H), 4.31 (ddd, J = 15.9, 10.7, 6.3 Hz, 3H), 2.81 (s, 1H), 2.42-2.26 (m, 2H), 2.21 (d, J = 14.7 Hz, 1H), 2.16-2.06 (m, 1H)ppm. |
| PA3018 | ¹H NMR (400 MHz, DMSO) δ 10.62 (s, 1H), 7.68 (s, 1H), 7.41 (d, J = 8.7 Hz, 1H), 7.38-7.26 (m, 2H), 6.47 (s, 2H), 5.87 (d, J = 10.9 Hz, 1H), 5.39 (s, 1H), 5.22 (s, 1H), 5.15 (d, J = 3.0 Hz, 1H), 4.64 (s, 2H), 4.55-4.41 (m, 1H), 4.26 (dd, J = 17.1, 7.2 Hz, 3H), 2.78 (s, 1H), 2.37 (dd, J = 35.1, 9.2 Hz, 2H), 2.12 (dd, J = 21.4, 12.7 Hz, 2H)ppm. |

TABLE 2-continued

NMR data on the compounds prepared in the examples were shown in the following table

| Number | NMR Data |
|---|---|
| PA3019 | $^1$H NMR (400 MHz, DMSO) δ 10.62 (s, 1H), 7.72 (s, 1H), 7.68 (d, J = 7.4 Hz, 1H), 7.48 (dd, J = 6.5, 1.4 Hz, 2H), 6.45 (s, 2H), 5.73 (d, J = 10.9 Hz, 1H), 5.39 (t, J = 9.2 Hz, 1H), 5.22 (s, 1H), 5.15 (s, 1H), 4.66 (s, 1H), 4.60-4.41 (m, 2H), 4.34-4.17 (m, 3H), 2.78 (s, 1H), 2.37-2.23 (m, 2H), 2.18 (d, J = 14.7 Hz, 1H), 2.13-2.03 (m, 1H)ppm. |
| PA3020 | $^1$H NMR (400 MHz, DMSO) δ 10.58 (s, 1H), 7.68 (s, 1H), 7.63 (d, J = 6.6 Hz, 1H), 7.35 (s, 1H), 7.19 (d, J = 6.8 Hz, 1H), 6.42 (s, 2H), 5.86 (d, J = 11.5 Hz, 1H), 5.38 (s, 1H), 5.20 (s, 1H), 5.13 (s, 1H), 4.65 (s, 1H), 4.61 (s, 1H), 4.54-4.40 (m, 1H), 4.23 (d, J = 17.0 Hz, 3H), 2.77 (s, 1H), 2.36-2.27 (m, 1H), 2.17-1.96 (m, 3H)ppm. |
| PA3022 | $^1$H NMR (400 MHz, DMSO) δ 10.58 (s, 1H), 7.68 (d, J = 4.1 Hz, 1H), 7.61-7.43 (m, 2H), 7.33 (s, 1H), 6.42 (s, 2H), 5.72 (d, J = 10.9 Hz, 1H), 5.39 (t, J = 9.0 Hz, 1H), 5.22 (s, 1H), 5.13 (d, J = 3.2 Hz, 1H), 4.65 (s, 1H), 4.61-4.40 (m, 2H), 4.36-4.16 (m, 3H), 2.78 (s, 1H), 2.36-2.22 (m, 2H), 2.17 (d, J = 14.6 Hz, 1H), 2.12-2.03 (m, 1H)ppm. |
| PA3023 | $^1$H NMR (400 MHz, DMSO) δ 10.59 (s, 1H), 7.76-7.66 (m, 2H), 7.65-7.56 (m, 1H), 7.49 (t, J = 7.9 Hz, 1H), 6.43 (s, 2H), 6.03-5.85 (m, 1H), 5.40 (t, J = 9.0 Hz, 1H), 5.24 (s, 1H), 5.16 (d, J = 3.0 Hz, 1H), 4.71-4.58 (m, 2H), 4.56-4.41 (m, 1H), 4.31 (ddd, J = 19.0, 10.7, 6.3 Hz, 3H), 2.80 (s, 1H), 2.31 (ddd, J = 18.3, 13.2, 7.4 Hz, 3H), 2.16-2.01 (m, 1H)ppm. |
| PA3024 | $^1$H NMR (400 MHz, DMSO) δ 10.59 (s, 1H), 7.72 (d, J = 2.0 Hz, 1H), 7.70 (s, 1H), 7.66-7.60 (m, 1H), 7.54 (dd, J = 8.5, 2.0 Hz, 1H), 6.42 (s, 2H), 5.88 (d, J = 10.6 Hz, 1H), 5.39 (t, J = 8.9 Hz, 1H), 5.23 (s, 1H), 5.15 (d, J = 3.2 Hz, 1H), 4.64 (dd, J = 12.7, 8.7 Hz, 2H), 4.50 (d, J = 16.8 Hz, 1H), 4.29 (ddd, J = 16.8, 10.4, 3.3 Hz, 3H), 2.79 (s, 1H), 2.37-2.16 (m, 3H), 2.09 (t, J = 10.5 Hz, 1H)ppm. |
| PA3026 | $^1$H NMR (400 MHz, DMSO) δ 10.58 (s, 1H), 7.71 (s, 1H), 7.69 (s, 1H), 7.46 (dd, J = 8.3, 1.9 Hz, 1H), 6.42 (s, 2H), 5.75 (d, J = 10.6 Hz, 1H), 5.39 (s, 1H), 5.22 (s, 1H), 5.14 (d, J = 3.2 Hz, 1H), 4.66 (s, 1H), 4.53 (d, J = 15.6 Hz, 2H), 4.36-4.17 (m, 3H), 2.78 (s, 1H), 2.37-2.18 (m, 3H), 2.10 (d, J = 7.5 Hz, 1H)ppm. |

Example 24: Evaluation of In-Vitro Metabolism in Liver Microsomes of Human, Mouse and Rat Assay Method:

1) Reagent Sources

Human liver microsomes (HLM) were purchased from IVT (In Vitro Technologies) (Product No. X008070, Batch No. SSP). Rat liver microsomes (RLM) were purchased from BD with a batch number of 16298, and mice liver microsomes (MLM) were purchased from Research Institute for Liver Diseases (Shanghai) Co., Ltd. (RILD), with a batch number of BQNI.

The test compounds PA3001, PA3002, PA3003, and PA3004 were synthesized by Zhejiang Palo Alto Pharmaceuticals, Inc., and dissolved in methanol (from Sinopharm Chemical Reagent Co., Ltd.) to prepare storage solutions at a concentration of 25 mM.

2) Reaction Process

The enzymatic reaction was carried out in a 100 mM KH2PO4 buffer solution (pH 7.4), with a test compound at a concentration of 25 μM, human liver microsomes at a concentration of 2 mg/ml, and NADPH at a concentration of 2 mM. The reaction was initiated by NADPH which was added last. After the reaction was carried out for 5 min in a constant-temperature shaking water bath kettle, methanol at a volume of 1.5 times that of the reaction mixture was added immediately to terminate the reaction.

) Sample Processing and Analysis Methods

I. Sample Pretreatment:

Each sample was centrifuged at a maximum speed of 13,600 rpm for 20 minutes using an Eppendorf tabletop centrifuge. The supernatant was taken, and was blow-dried by a nitrogen blower and then re-dissolved in mobile phase A (0.1% formic acid (v/v) in water).

II. Liquid Phase Gradient:

| Time (minute) | Mobile Phase A (0.1% FA in H$_2$O) | Mobile Phase B (Acetonitrile) |
|---|---|---|
| 0 | 99 | 1 |
| 1.1 | 90 | 10 |
| 1.5 | 20 | 80 |
| 2.5 | 99 | 1 |

Analysis Column: Waters, Acquity UPLC HSS T3 Column
Flow Rate: 0.5 ml/min
Column Temperature: 40 degrees Celsius
III. Mass Spectrometry Condition
Ion Source: Electrospray Ionization Source
Ion Mode: Positive Ion Mode
Capillary Voltage: 3.0 kV
Temperature: 500° C.
Desolvation Gas Flow Rate: 100 LIh
Scan Time: 0.025 s
Cone Voltage: 40 V
Collision Energy: 18 eV
Q1 (m/z): 358
Q3 (m/z): 152

TABLE 3

Rate of Release of Monophosphate Product ETVMP by In-vitro Metabolism of the Compounds in Liver Microsomes

| Activation Rate pmol/min/mg HLM | Human HLM | Mice HLM | Rat HLM |
|---|---|---|---|
| PA3001 | 402.2 ± 75.1 | 375.8 ± 14.5 | 240.6 ± 52.6 |
| PA3002 | 481.6 ± 3.5 | ND | ND |
| PA3003 | 57.7 ± 3.7 | 107.7 ± 0.3 | 56.9 ± 2.5 |
| PA3004 | 507.8 ± 19.6 | 520.5 ± 5.2 | 276.5 ± 18.6 |

Note:
ND = Not Determined

Result Analysis:

The compounds PA3001, PA3003, and PA3004 were all activated in vitro by human, rat, and mouse liver microsomes into monophosphate metabolites ETVMP. PA3002 and PA3004 were activated by human liver microsomes into monophosphate metabolites ETVMP with an efficiency significantly greater than that of the comparative compound PA3001. Different compounds were converted at significantly different rates (Table 3), wherein PA3004 was converted at the highest rate in each of the species.

Example 25: Evaluation of In-Vitro Metabolism in Human Liver Microsomes

Assay Method:
1) Reagent Sources

Human liver microsomes (HLM) were purchased from IVT (In Vitro Technologies) (Product No. X008070, Batch No. IQF).

The test compounds PA3001, PA3002, PA3003, PA3004, PA3010, PA3011, PA3012A, PA3013, PA3014, PA3016, PA3017, PA3018, PA3019, PA3020, PA3022, PA3023, PA3024, and PA3026 were synthesized by Zhejiang Palo Alto Pharmaceuticals, Inc., and dissolved in methanol (from Sinopharm Chemical Reagent Co., Ltd.) to prepare storage solutions at a concentration of 25 mM.

2) Reaction Process

The enzymatic reaction was carried out in a 100 mM $KH_2PO_4$ buffer solution (pH 7.4), with a test compound at a concentration of 25 μM, human liver microsomes at a concentration of 2 mg/ml, and NADPH at a concentration of 2 mM. The reaction was initiated by NADPH which was added last. After the reaction was carried out for 5 min in a constant-temperature shaking water bath kettle, methanol at a volume of 1.5 times that of the reaction mixture was added immediately to terminate the reaction.

3) Sample Processing and Analysis Methods

I. Sample Pretreatment:

Each sample was centrifuged at a maximum speed of 13,600 rpm for 20 minutes using an Eppendorf tabletop centrifuge. The supernatant was taken, and was blow-dried by a nitrogen blower and then re-dissolved in mobile phase A (0.1% formic acid (v/v) in water).

II. Liquid Phase Gradient:

| Time (minute) | Mobile Phase A (0.1% FA in $H_2O$) | Mobile Phase B (Acetonitrile) |
| --- | --- | --- |
| 0 | 99 | 1 |
| 1.1 | 90 | 10 |
| 1.5 | 20 | 80 |
| 2.5 | 99 | 1 |

Analysis Column: Waters, Acquity UPLC HSS T3 Column
Flow Rate: 0.5 ml/min
Column Temperature: 40 degrees Celsius
III. Mass Spectrometry Condition
Ion Source: Electrospray Ionization Source
Ion Mode: Positive Ion Mode
Capillary Voltage: 3.0 kV
Temperature: 500° C.
Desolvation Gas Flow Rate: 100 L/h
Scan Time: 0.025 s
Cone Voltage: 40 V
Collision Energy: 18 eV
Q1 (m/z): 358
Q3 (m/z): 152

TABLE 4

Rate of Release of Monophosphate Product ETVMP by In-vitro Metabolism of the Compounds in Human Liver Microsomes

| Compound | Activation Rate pmol/min/mg HLM |
| --- | --- |
| PA3001 | 40.49 ± 2.95 |
| PA3002 | 47.95 ± 1.45 |
| PA3003 | 24.46 ± 0.87 |
| PA3004 | 62.17 ± 0.28 |
| PA3010 | 26.50 ± 3.02 |
| PA3011 | 36.04 ± 0.68 |
| PA3012 | 12.36 ± 0.55 |
| PA3013 | 14.74 ± 2.27 |
| PA3014 | 17.67 ± 0.22 |
| PA3016 | 122.48 ± 1.13 |
| PA3017 | 188.37 ± 0.88 |
| PA3018 | 26.70 ± 5.44 |
| PA3019 | 18.43 ± 2.08 |
| PA3020 | 10.72 ± 0.13 |
| PA3022 | 10.31 ± 0.01 |
| PA3023 | 14.84 ± 0.23 |
| PA3024 | 50.81 ± 2.89 |
| PA3026 | 10.73 ± 0.10 |

Result Analysis:

All the compounds could be activated in vitro by human liver microsomes into the monophosphate metabolite ETVMP. Different compounds were converted at significantly different rates (Table 4). PA3017, PA3016, and PA3004 were activated by human liver microsomes into the monophosphate metabolite ETVMP with an efficiency significantly greater than that of the comparative compound PA3001, and were converted at rates that were 4.6 times, 3.0 times, and 1.5 times that of PA3001, respectively.

Example 26: Experiment for Distribution of Compounds in Tissues 26.1 Method:

26.1.1 Animal Experiment

Male SD (Sprague-Dawley) rats, weighing 180 to 300 g, were provided by Shanghai Xipuer-Beikai Experimental Animal Co., Ltd. The male animals were acclimatized to the environment for more than 3 days, and fasted for 12 hours overnight before the experiment, but were allowed to drink water. Solutions were prepared from PA3001, PA3002, PA3003, PA3004, and entecavir (Cremophor EL:ethanol:saline=10:10:80 V/V/V), respectively. Before administration, the animals were checked to determine whether their body weights met the experimental requirements. Twelve rats were selected for grouping, two rats in each group. The drug solutions were administered intragastrically to the rats in an amount of 0.036 mmol/kg. The rats were euthanized with carbon dioxide gas and samples were collected, at 0.5 h, 1 h, 3 h, 6 h, 12 h, and 24 h, respectively.

26.1.2. Measurement of Contents of Monophosphate Metabolite ETVMP and Dephosphorylated Metabolite ETV in Biological Samples Sample Pretreatment Blood was drawn from the hearts of the rats and stored in heparin anticoagulation tubes, which were centrifuged at 6,000 rpm for 5 min at 4° C. The supernatant plasma was taken, to which 10% trichloroacetic acid (containing PMPA as an internal standard, at a concentration of 100 ng/mL) was immediately added as a precipitant at a volume 5 times that of the plasma, to obtain plasma sample solutions. Appropriate amounts of liver and brain tissue samples of the rats were weighed on ice and stored in homogenization tubes, to each of which 10% trichloroacetic acid was immediately added as a precipitant at a volume 5 times that of the sample as described above. Two ceramic beads were added to each of the homogenization tubes for homogenization to obtain tissue homogenate samples.

100 μL of each biological sample was taken, placed in a 1.5 mL test tube, and centrifuged for 5 min. 20 μL of the supernatant was taken and mixed uniformly with 180 μL of water and then analyzed by LC-MS/MS.

Chromatographic Condition

LC-MS/MS-AJ (Triple Quad 5500, AB SCIEX) was used for analysis of the samples. Chromatographic Column: Acquity UPLC HSS T3 (2.1×50 mm, 1.8 μm); Column Temperature: 40° C.; Flow Rate: 0.5 mL/min. Mobile Phase A: 0.1% formic acid in water, Mobile Phase B: Acetonitrile Solution. The samples were separated by gradient elution according to the procedure shown in Table 5.

TABLE 5

Liquid Phase Elution Gradient Condition for ETVMP and ETV

| Time (min) | Mobile Phase B (%) |
|---|---|
| 0 | 1 |
| 1.1 | 10 |
| 1.5 | 80 |
| 2.5 | 1 |

Mass Spectrometry Condition

The mass spectrometry was performed with an electrospray ionization source (Turbo Ionspray) as an ion source, in a positive ion mode, at a capillary voltage of 3.0 kV, at a temperature of 500° C., and at a desolvation gas flow of 1000 L/h. The scanning time, cone voltage, collision energy, and the ion reaction for quantitative analysis were shown in Table 6 below:

TABLE 6

Mass Spectrometry Condition for ETVMP and ETV

| Analyte | Q1 (m/z) | Q3 (m/z) | Dwell (s) | Cone (V) | Collision (V) |
|---|---|---|---|---|---|
| ETVMP | 358 | 152 | 0.025 | 40 | 18 |
| ETV | 278 | 152 | 0.025 | 40 | 18 |
| PMPA (IS) | 288 | 176 | 0.025 | 40 | 25 |

Note:
The ETVMP samples were less stable at room temperature and thus should be operated on ice and added immediately with a precipitant.

26.1.3. Data Analysis

The concentration of the metabolite from each of the compounds in the liver was plotted as a function of time on a bar chart. The area under the curve of ETVMP and ETV concentration in tissue as a function of time (AUCO-t) was fitted and calculated according to the Log-linear trapezoidal method in a non-compartmental model using WinNonLin6.2.1 (Pharsight, CA).

26.2 Experimental Results

The results of release of ETVMP and ETV from PA3001, PA3002, PA3003, PA3004, PA3017, and entecavir were summarized in Table 7.

TABLE 7

Amounts ($AUC_{0-24\,h}$, h · nmol/g, concentration/tissue weight) of Monophosphate Metabolite ETVMP and Dephosphorylated Metabolite ETV Exposed in Liver, Brain Tissue, and Plasma within 24 hours after Intragastric Administration of 0.036 mmol/kg of PA3001, PA3002, PA3003, PA3004, and Entecavir to the Rats

| | Liver | | Brain Tissue | | Plasma | | Ratio ETVMP in Liver/ETV in Blood |
|---|---|---|---|---|---|---|---|
| | ETV | ETVMP | ETV | ETVMP | ETV | ETVMP | |
| ETV | 228.1 | 16.6 | 6.7 | 3.5 | 32.2 | 0.55 | 0.51 |
| PA3001 | 41.7 | 16.2 | N.D. | 0.2 | 1.30 | 0.17 | 12.46 |
| PA3002 | 15.3 | 8.1 | N.D. | N.D. | 0.25 | 0.03 | 32.40 |
| PA3003 | 70.6 | 18.9 | 0.8 | 1.1 | 4.79 | 0.19 | 3.94 |
| PA3004 | 27.0 | 11.6 | N.D. | N.D. | 0.75 | 0.09 | 15.47 |
| PA3017 | 16.8 | 9.0 | N.D. | N.D. | 0.58 | 0.08 | 15.52 |

N.D. = Not detectable (representing a concentration in the corresponding organ or tissue less than 5 nmol/g or 5 nmol/mL)

26.2.1 Distribution of Metabolites in Liver, Plasma, and Brain Tissues

Figure 2:
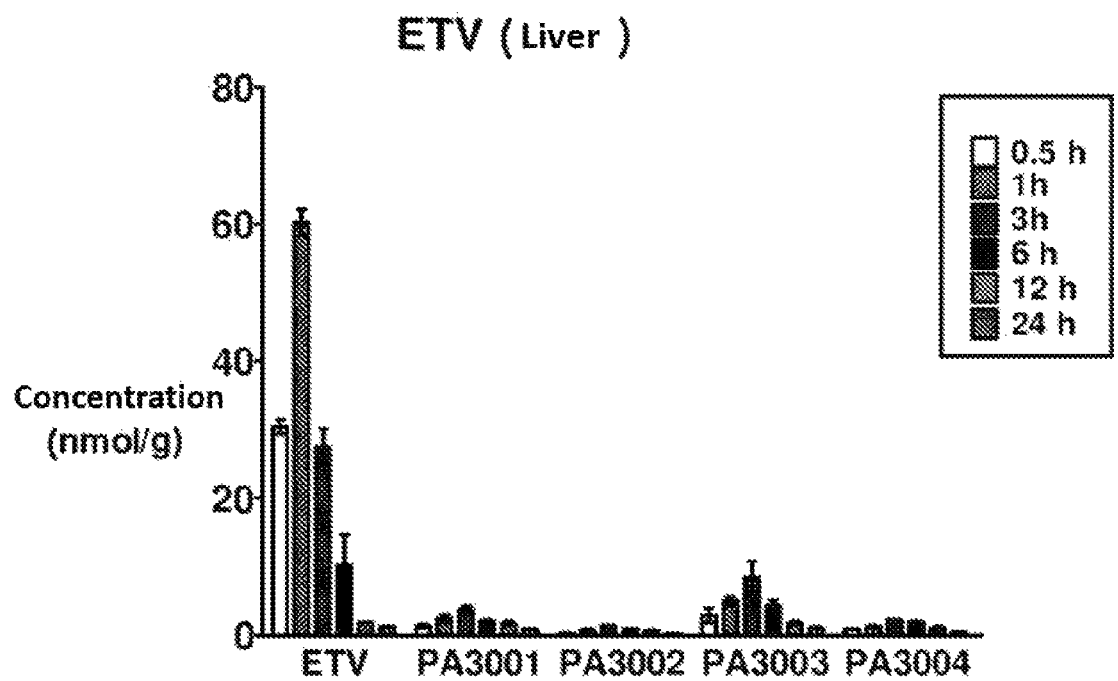
FIG. 2 is a bar chart showing concentrations (nmol/g, molar concentration/tissue weight) of ETV in the liver over time after intragastric administration of 0.036 mmol/kg of PA3001, PA3002, PA3003, PA3004, PA3017, and entecavir to rats.
Figure 3:
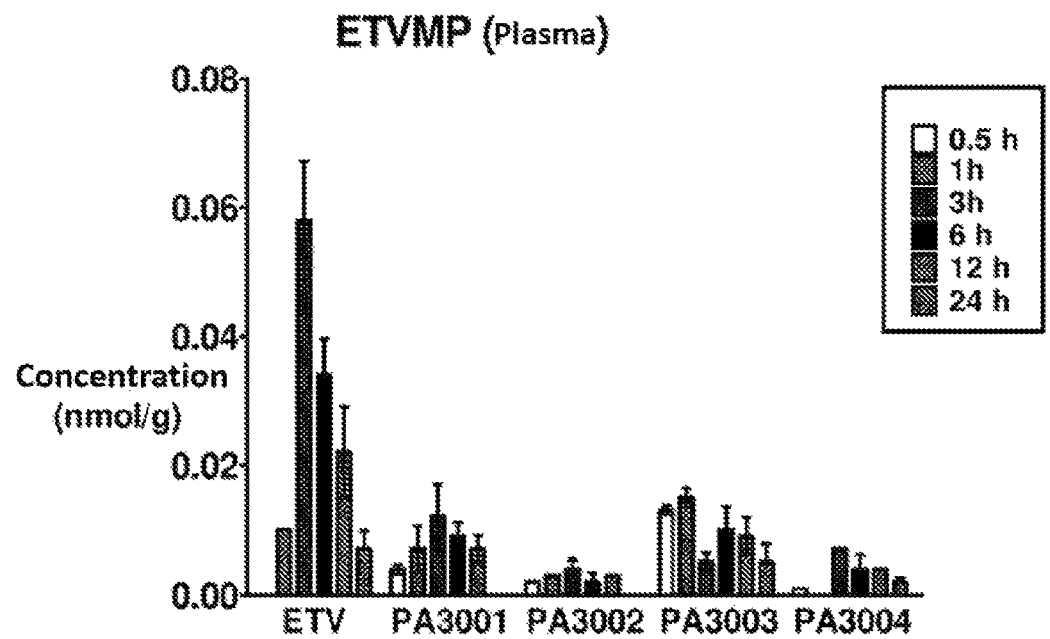
FIG. 3 is a bar chart showing concentrations (nmol/g, molar concentration/tissue weight) of active monophosphate molecules ETVMP in plasma over time after intragastric administration of 0.036 mmol/kg of PA3001, PA3002, PA3003, PA3004, PA3017, and entecavir to rats.
Figure 4:
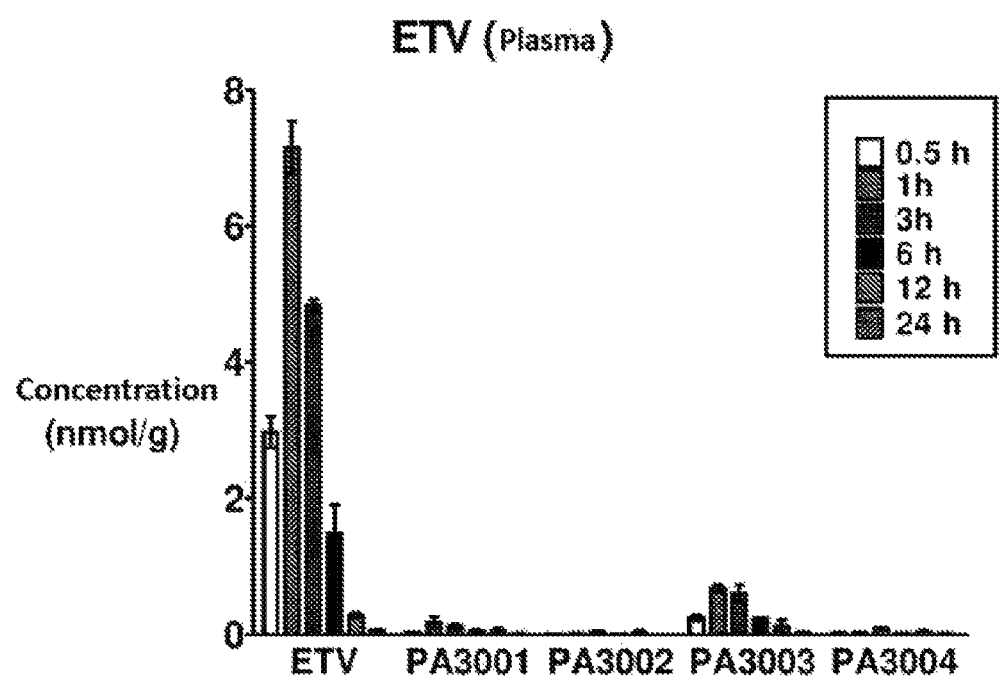
FIG. 4 is a bar chart showing concentrations (nmol/g, molar concentration/tissue weight) of ETV in plasma over time after intragastric administration of 0.036 mmol/kg of PA3001, PA3002, PA3003, PA3004, PA3017, and entecavir to rats.
Figure 5:
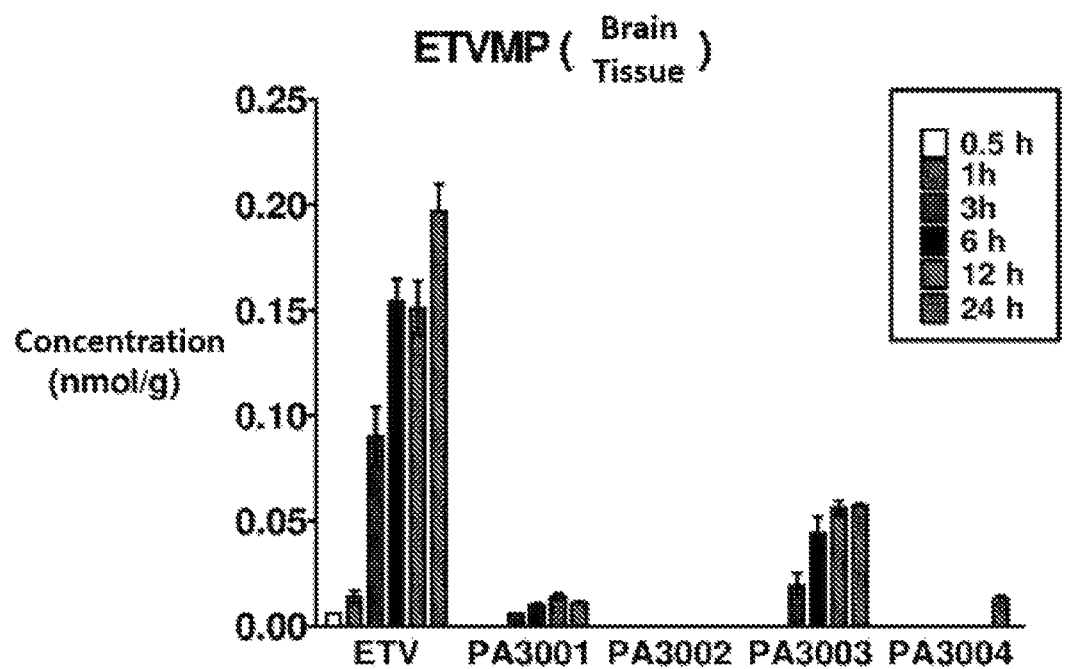
FIG. 5 is a bar chart showing concentrations (nmol/g, molar concentration/tissue weight) of active monophosphate molecules ETVMP in brain tissues over time after intragastric administration of 0.036 mmol/kg of PA3001, PA3002, PA3003, PA3004, PA3017, and entecavir to rats.
Figure 6:
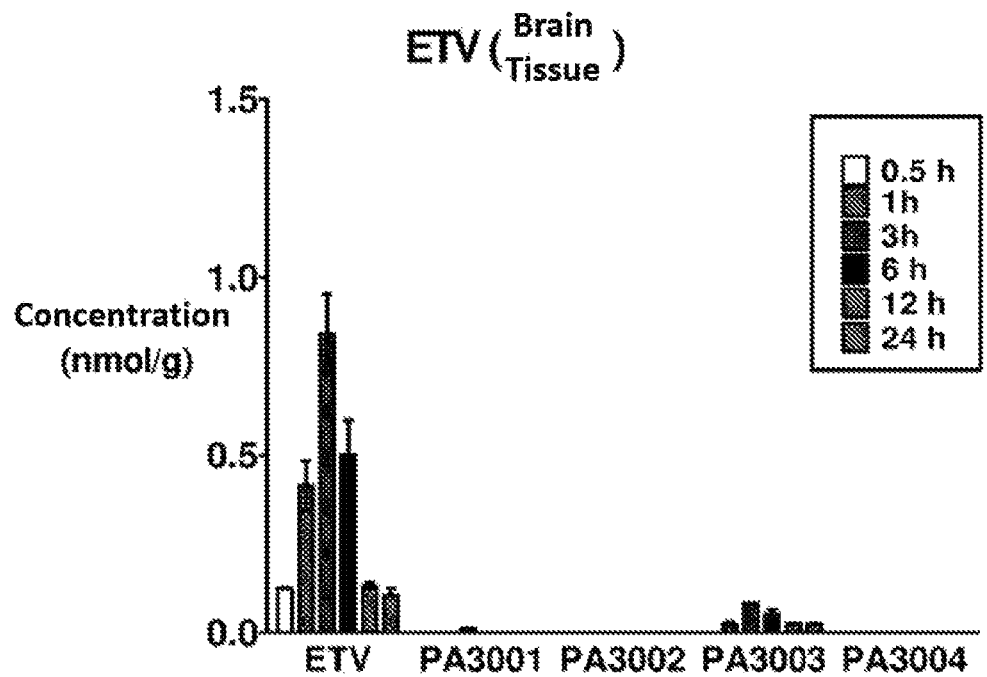
FIG. 6 is a bar chart showing concentrations (nmol/g, molar concentration/tissue weight) of ETV in brain tissues over time after intragastric administration of 0.036 mmol/kg of PA3001, PA3002, PA3003, PA3004, PA3017, and entecavir to rats.

After the test drugs were orally (intragastrically) administered to the SD rats in an amount of 0.036 mmol/kg, the results of their distributions in liver tissue showed that PA3001, PA3002, PA3003, PA3004, and PA3017 were metabolized to release active molecules ETVMP inhibiting the polymerase of hepatitis B virus at a level slightly lower than or equal to ETV at the corresponding time point (FIG. 1), while PA3001. PA3002, PA3003, PA3004, and PA3017 generates the dephosphorylated metabolite ETV in the liver at a level much lower than ETV (FIG. 2). This indicated that ETVMP generated by metabolism of the prodrugs was not likely to be reversely converted and metabolized to ETV, thus the efficacy of the prodrugs was ensured. The compound of formula II was directly enzymatically catalyzed by CYP3A4 in the liver to release the monophosphate product ETVMP. The conversion of ETV into monophosphate was a rate-limiting step, ETVMP was not likely to be reversely converted and metabolized to ETV. Therefore, the compound of formula II could increase the distribution ratio of the active metabolite in the liver and reduce the distribution ratio of the metabolite in plasma, brain tissue, and other tissues.

After the test drugs were orally (intragastrically) administered to the SD rats in an amount of 0.036 mmol/kg, the results of their distributions in blood and brain tissue showed that each of PA3001, PA3002, PA3003, PA3004, and PA3017 was metabolized to release ETVMP and ETV at much lower levels than ETV at the corresponding time point (FIGS. 3, 4, 5, and 6). This indicated that ETV could pass through the blood and brain barrier. ETV itself and its metabolite ETVMP were the active molecules causing neurotoxicity in the brain.

These active molecules were not detected in brain samples of rats orally administered with PA3004 and PA3017 (Table 7) by using the established LC-MS/MS detection method (with a lower limit of detection LOD=5 nmol/g or 5 nmol/mL). In the blood, PA3004 and PA3017 released ETVMP at levels of 16.4% and 14.5% relative to ETV, respectively; and PA3004 and PA3017 released ETV at levels that were respectively 2.3% and 1.8% relative to ETV and that were also lower than that of Comparative Example PA3001.

The liver targeting effects of the compounds could be reflected by a ratio of the AUC of ETVMP in liver to the AUC of ETV in blood (a liver targeting index). PA3004 and PA3017 respectively showed liver targeting indexes of 15.52 and 15.47, which were significantly greater than those of PA3001 and ETV (having liver targeting indexes of 12.46 and 0.51, respectively). These results indicated that the compounds modified with liver specific delivery groups significantly reduced the distributions of the active molecules ETVMP and ETV in blood and brain compared with ETV at the same dosage. PA3017 and PA3014 could ameliorate the common adverse effects clinically caused by ETV, including headache, fatigue, dizziness, nausea, and so on.

In summary, the compounds of formula I and formula II of the present disclosure have higher activity and higher delivery specificity to liver tissue, therefore the compounds can be used therapeutically in a less amount, with higher safety and lower toxic and side effects.

All documents mentioned in the present disclosure are cited in the present disclosure as if each document was individually cited as reference. Besides, it should be understood that various changes or modifications of the present disclosure could be made by those skilled in the art after reading the above teachings of the present disclosure, and these equivalents also fall within the scope defined by the appended claims of the present disclosure.

What is claimed is:

1. A compound of formula (I), or an optical isomer, a pharmaceutically acceptable salt, a hydrate or a solvate thereof:

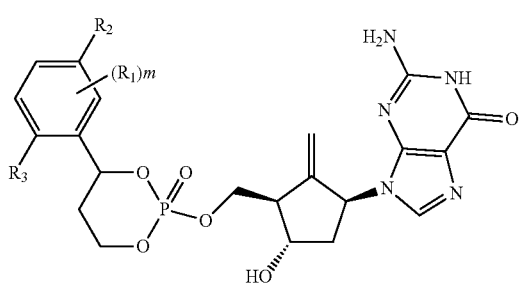

wherein
$R_2$ is Cl and $R_3$ is F; or $R_2$ is Cl and $R_3$ is Cl; or $R_2$ is F and $R_3$ is Cl; and
m is 0.

2. The compound according to claim 1, or an optical isomer, a pharmaceutically acceptable salt, a hydrate or a solvate thereof, wherein a salt of the compound of formula (I) is a pharmaceutically acceptable salt formed from the compound of formula (I) with an inorganic acid or an organic acid, or formed from the compound of formula (I) with a base, and the compound of formula (I) or the salt thereof is amorphous or crystalline.

3. A pharmaceutical composition, comprising a therapeutically effective amount of the compound, or an optical isomer, a pharmaceutically acceptable salt, a hydrate or a solvate thereof of claim 1 and a pharmaceutically acceptable adjuvant, diluent, or carrier.

4. A method for treating hepatitis B virus infection, in a subject, comprising:
administering to the subject an effective amount of the compound, or an optical isomer, a pharmaceutically acceptable salt, a hydrate or a solvate thereof of claim 1.

5. A method according for preparing the compound of claim 1, wherein the compound of formula (I) is prepared through the step of:

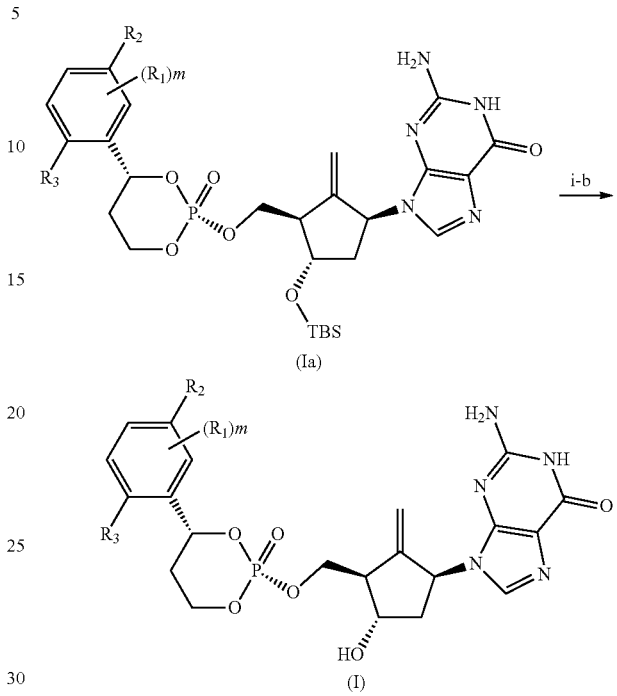

(i-b) removing TBS from a compound of formula (Ia) in an inert solvent to form the compound of formula (I), wherein each group in the formulas is defined in the same manner as in claim 1;
wherein the compound of formula (Ia) is prepared through the step of:

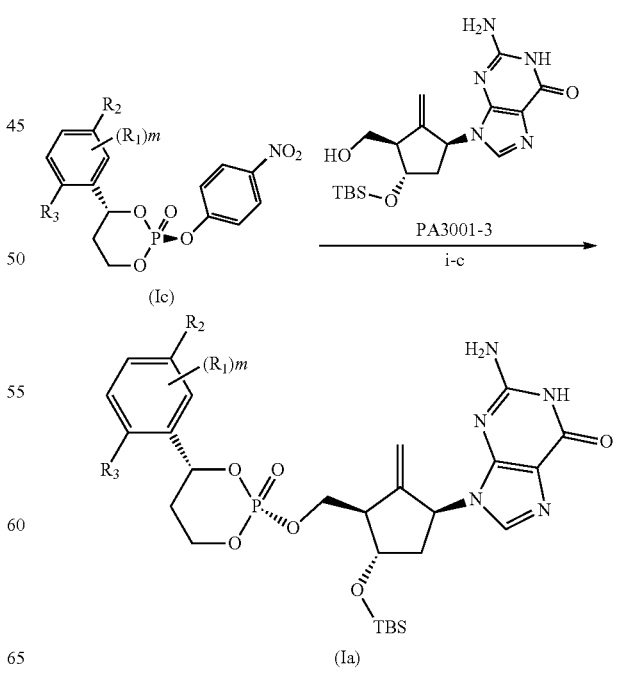

(i-c) subjecting a compound of formula (Ic) and PA3001-3 to a substitution reaction in an inert solvent to obtain the compound of formula (Ia).

* * * * *